US011365229B2

(12) United States Patent
Szymkowski et al.

(10) Patent No.: US 11,365,229 B2
(45) Date of Patent: Jun. 21, 2022

(54) METHODS OF TREATING NEUROLOGICAL DISEASES

(71) Applicant: Xencor, Inc., Monrovia, CA (US)

(72) Inventors: David Szymkowski, Monrovia, CA (US); Malu Tansey, Decatur, GA (US); Lesley Probert, Athens (GR)

(73) Assignee: XENCOR, INC., Monrovia, CA (US)

( * ) Notice: Subject to any disclaimer, the term of this patent is extended or adjusted under 35 U.S.C. 154(b) by 0 days.

(21) Appl. No.: 14/427,279

(22) PCT Filed: Sep. 10, 2013

(86) PCT No.: PCT/US2013/059071

§ 371 (c)(1),
(2) Date: Mar. 10, 2015

(87) PCT Pub. No.: WO2014/040076

PCT Pub. Date: Mar. 13, 2014

(65) Prior Publication Data

US 2015/0239951 A1 Aug. 27, 2015

Related U.S. Application Data

(60) Provisional application No. 61/699,230, filed on Sep. 10, 2012, provisional application No. 61/826,922, filed on May 23, 2013.

(51) Int. Cl.

| | |
|---|---|
| ***C07K 14/525*** | (2006.01) |
| ***A61K 38/19*** | (2006.01) |
| ***A61K 38/00*** | (2006.01) |
| ***A61K 48/00*** | (2006.01) |

(52) U.S. Cl.

CPC .......... *C07K 14/525* (2013.01); *A61K 38/191* (2013.01); *A61K 38/00* (2013.01); *A61K 48/00* (2013.01)

(58) Field of Classification Search

CPC .... C07K 14/525; A61K 38/191; A61K 38/00; A61K 48/00; A61P 25/28; A61P 25/24; A61P 25/16; A61P 25/00

See application file for complete search history.

(56) References Cited

U.S. PATENT DOCUMENTS

| | | | | |
|---|---|---|---|---|
| 6,177,077 B1 * | 1/2001 | Tobinick | C07K 16/241 424/134.1 |
| 7,244,823 B2 * | 7/2007 | Dahiyat | A61K 38/191 435/335 |
| 7,642,340 B2 * | 1/2010 | Desjarlais | C07K 1/1077 424/85.1 |
| 7,687,461 B2 * | 3/2010 | Desjarlais | A61K 38/191 424/85.1 |
| 2008/0187509 A1 | 8/2008 | Desjarlais et al. | |
| 2012/0088713 A1 | 4/2012 | Lane et al. | |

FOREIGN PATENT DOCUMENTS

WO WO 2006113487 A1 * 10/2006 .......... A61K 38/191

OTHER PUBLICATIONS

McCandless et al. IL-1R signaling within the central nervous system regulates CXCL12 expression at the blood-brain barrier and disease severity during experimental autoimmune encephalomyelitis. J Immunol. Jul. 1, 2009;183(1):613-20. doi: 10.4049/jimmunol.0802258. Epub Jun. 17, 2009.*

Donahue et al. Apolipoprotein E, amyloid-beta, and blood-brain barrier permeability in Alzheimer disease. J Neuropathol Exp Neurol. Apr. 2008;67(4):261-70.*

Brambilla et al., "Inhibition of soluble tumour necrosis factor is therapeutic in experimental autoimmune encephalomyelitis and promtes axon perservation and remyelination," Brain, vol. 134, No. 9, pp. 2736-2754, (2011).

Harms et al., "Delayed Dominant-Negative TNF Gene Therapy Halts Prgressive Loss of Nigral Dopaminergic Neurons in a Rat Model of Parkinson's Disease," American Society of Gene & Cell Therapy, pp. 1-8, (2010).

McAlpine et al., "Inhibition of soluble TNF signaling in a mouse model of Alzheimer's disease prevents pre-plaque amyloid-associated neuropathology," Neurobiology of Disease, vol. 34, pp. 163-177, (2009).

McCoy et al., "Blocking Soluble Tumor Necrosis Factor Signaling with Dominant-Negative Tumor Necrosis Factor Inhibitor Attentuates Loss of Dopaminergic Neurons in Models of Parkinson's Disease," J. of Neuroscience, vol. 26(37), pp. 9365-9375, (2006).

Taoufik et al., "Transmembrane tumour necrosis factor is neuroprotective and regulates experimental autoimmune encephalomyelitis via neuronal nuclear factor-B," Brain, vol. 134, No. 9, pp. 2722-2735, (2011).

William A. Banks, "Drug delivery to the brain in Alzheimer's disease: Consideration of the blood-brain barrier," Advanced Drug Delivery Reviews, vol. 64, pp. 629-639 (2012).

Hofstetter et al., "Pertussis Toxin Modulates the Immune Response to Neuroantigens Injected in Incomplete Freund's Adjuvant: Induction of Th1 Cells and Experimental Autoimmune Encephalomyelitis in the Presence of High Frequencies of Th2 Cells," J. of Immunology, vol. 169, pp. 117-125 (2002).

Kontermann et al., "Antagonists of TNF action: clinical experience and new developments," Expert Opinion on Drug Discovery, vol. 4, No. 3, pp. 279-292 (2009).

Sama et al., "Inhibition of Soluble Tumor Necrosis Factor Ameliorates Synaptic Alterations and Ca2+ Dysregulation in Aged Rates," Plos One, vol. 7, No. 5, pp. e38170 1-10 (2012).

Steed et al., "Inactivation of TNF signaling by rationally designed dominant-negative TNF variants," Science, vol. 301, No. 5641, pp. 1895-1898 (2003).

(Continued)

*Primary Examiner* — Gregory S Emch

(74) *Attorney, Agent, or Firm* — Coastal Patent Law Group, P.C.; Joshua S. Schoonover

(57) ABSTRACT

The present disclosure is directed to a method of treating neurological disorder comprising peripheral administration to a patient in need thereof a DN-TNF polypeptide that inhibits the activity of soluble TNF- but not transmembrane TNF-α.

8 Claims, 10 Drawing Sheets

Specification includes a Sequence Listing.

(56) References Cited

OTHER PUBLICATIONS

Edward Tobinick, Deciphering the Physiology Underlying the Rapid Clinical Effects of Perispinal Etanercept in Alzheimer's Disease, Current Alzheimer Research, 2012, 99-109, vol. 9.

Christopher Rowland, Pfizer had clues its blockbuster drug could prevent Alzheimer's. Why didn't it tell the world?, https://www.washingtonpost.com/business/economy/pfizer-had-clues-its-blockbuster-drug-could-prevent-alzheimers-why-didnt-it-tell-the-world/2019/06/04/9092e08a-7a61-11e9-8bb7-0fc796cf2ec0_story.html?noredirect=on, Jun. 4, 2019.

Victoria Connor, Anti-TNF therapies: a comprehensive analysis of adverse effects associated with immunosupression. Rheumatology International, Springer Verlag, 2009, 31(3), pp. 327-337. 10.1007/s00296-009-1292-x. hal-00568316.

Fabiola Atzeni et al. Central nervous system involvement in rheumatoid arthritis patients and the potential implications of using biological agents. Best Practice & Research Clinical Rheumatology. 2018. 32. 500-510.

Evripidis Kaltsonoudis et al. Demyelination and other neurological adverse events after anti-TNF therapy. Autoimmun Rev. Jan. 2014;13(1):54-8. doi: 10.1016/j.autrev.2013.09.002. Epub Sep. 12, 2013. PMID: 24035809.

Maria Karamita et al. Therapeutic inhibition of soluble brain TNF promotes remyelination by increasing myelin phagocytosis by microglia. JCI Insight. 2017;2(8):e87455. https://doi.org/10.1172/jci.insight.87455.

Minna Yli-Karjanmaa et al. Topical Administration of a Soluble TNF Inhibitor Reduces Infarct Volume After Focal Cerebral Ischemia in Mice. Frontiers in Neuroscience. 2019. 13. 781.

https://www.sec.gov/Archives/edgar/data/1711754/000164033419000238/inmune_ex991.htm.

https://www.sec.gov/Archives/edgar/data/1711754/000121390021003480/ea133728ex99-1_inmunebio.htm.

* cited by examiner

```
1    atgcaccacc accaccacca cgtacgctcc tcctcccgca ctccgtccga caaaccggta
61   gctcacgtag tagctaaccc gcaggctgaa ggtcagctgc agtggctgaa ccgccgcgct
121  aacgctctgc tggctaacgg tgtagaactg cgcgacaacc agctggtagt accgtccgaa
181  ggtctgtacc tgatctactc ccaggtactg ttcaaaggtc agggttgtcc gtccactcac
241  gtactgctga ctcacactat ctcccgcatc gctgtatcct accagactaa agtaaacctg
301  ctgtccgcta tcaaatcccc gtgtcagcgc gaaactccgg aaggtgctga agctaaaccg
361  tggtacgaac cgatctacct gggtggtgta ttccagctgg aaaaaggtga ccgcctgtcc
421  gctgaaatca accgcccgga ctacctggac ttcgctgaat ccggtcaggt atacttcggt
481  atcatcgctc tgtga
```

(SEQ ID NO:1)

FIG. 1A

```
1    MHHHHHHVRS SSRTPSDKPV AHVVANPQAE GQLQWLNRRA NALLANGVEL RDNQLVVPSE
61   GLYLIYSQVL FKGQGCPSTH VLLTHTISRI AVSYQTKVNL LSAIKSPCQR ETPEGAEAKP
121  WYEPIYLGGV FQLEKGDRLS AEINRPDYLD FAESGQVYFG IIAL
```

(SEQ ID NO:2)

FIG. 1B

| Wild-type TNF amino acid | Wild-type TNF amino acid number | Mutants created |
|---|---|---|
| Q | 21 | R |
| N | 30 | D |
| R | 31 | I, D, E |
| R | 32 | D, E, S |
| A | 33 | E |
| A | 35 | S |
| K | 65 | D, T, M, W, I, Q, S, N, V, E |
| G | 66 | Q, K |
| Q | 67 | D, W, Y, R, K, S |
| A | 111 | R, E |
| K | 112 | D, E |
| Y | 115 | Q, K, E, N, R, F, H, M, L, I, W, D, T, S |
| D | 140 | R, K |
| D | 143 | E, N, Q, S, R, K |
| F | 144 | N |
| A | 145 | R, D, K, N, H, T, Q, E, Y, M, S, F |
| E | 146 | N, K, R, S |
| S | 147 | R |

ALSO MADE DOUBLE MUTANTS K65E/D143K, K65E/D143R, K65D/D143K AND K65D/D143R

Val Arg Ser Ser Ser Arg Thr Pro Ser Asp Lys Pro Val Ala His Val Val Ala Asn Pro Gln Ala Glu
Gly Gln Leu Gln Trp Leu Asn Arg Arg Ala Asn Ala Leu Leu Ala Asn Gly Val Glu Leu Arg Asp
Asn Gln Leu Val Val Pro Ser Glu Gly Leu Tyr Leu Ile Tyr Ser Gln Val Leu Phe Lys Gly Gln
Gly Cys Pro Ser Thr His Val Leu Leu Thr His Thr Ile Ser Arg Ile Ala Val Ser Tyr Gln Thr Lys
Val Asn Leu Leu Ser Ala Ile Lys Ser Pro Cys Gln Arg Glu Thr Pro Glu Gly Ala Glu Ala Lys Pro
Trp Tyr Glu Pro Ile Thr Leu Gly Gly Val Phe Gln Leu Glu Lys Gly Asp Arg Leu Ser Ala Glu Ile
Asn Arg Pro Asp Tyr Leu Asp Phe Ala Glu Ser Gly Gln Val Tyr Phe Gly Ile Ile Ala Leu

FIG. 10

METHODS OF TREATING NEUROLOGICAL DISEASES

FIELD OF INVENTION

The present invention relates generally to the peripheral administration of a TNF-α inhibitor, preferably a dominant negative TNF-α protein for the treatment of a neurological disorder associated with TNF-α.

BACKGROUND OF THE INVENTION

Treatment of neurological disorders is complicated by the fact that the majority of the underlying causes of the disorders are localized in the brain, which has proven recalcitrant to treatment save for complicated and risky direct administration of a therapeutic into the brain. Currently it is believed that the blood brain barrier proves an insurmountable obstacle that prevents peripherally delivered therapies from reaching their target in the brain.

The blood-brain barrier (BBB) is a structural system comprised of endothelial cells that functions to protect the central nervous system (CNS) from deleterious substances in the blood stream, such as bacteria, macromolecules (e.g., proteins) and other hydrophilic molecules, by limiting the diffusion of such substances across the BBB and into the underlying cerebrospinal fluid (CSF) and CNS. Therefore, it serves an important function. However, it also poses a significant obstacle to providing therapeutics to the brain, leaving those suffering from neurological disorders, including devastating neurodegenerative diseases lacking effective therapeutics.

Treatment of neurological diseases is further complicated by the complex signaling networks involved in neuronal regulation. For instance, therapeutics that are effective immunomodulators in the periphery are contraindicated for treatment of neuroinflammatory disorders. Currently marketed TNF-α inhibitors are labeled with a BLACK BOX WARNING specifically warning against treatment of neurological diseases because they cause demyelination resulting in worsening of the condition.

Although significant efforts to identify effective therapies have been undertaken, to date there is a dearth of such therapies. As such, there is a significant need to develop effective therapies to treat neurological disorders, such as neuroinflammatory and neurodegenerative diseases.

SUMMARY OF INVENTION

In contrast to the prior art intracranial administration of a TNF-α inhibitor to treat neurological disorders, demonstrated herein is the novel and unexpected finding that certain dominant negative TNF-α proteins (DN-TNF) have effects on the CNS and brain when administered peripherally. In an embodiment the effects are mediated via direct contact of the DN-TNF with the brain and/or CNS as the DN-TNF agents cross the blood brain barrier. Accordingly, provided herein is a method of treating a patient with a neurological disease comprising administering to the patient a therapeutically effective amount of a dominant negative TNF-α inhibitor, wherein said dominant negative TNF-α inhibitor is administered peripherally, i.e., not through the cranium or perispinally. Exemplary peripheral routes include, but are not limited to, enteral, topical, subcutaneous, intradermal, inhalational, parenteral, intramuscular, mucosal, intra-nasal, oral, vaginal, rectal, intravenous, intraarterial, intracardiac, intraosseal, intrathecal, intraperitoneal, intravesical, and intravitreal routes.

In one embodiment, the neurological disorder is associated with TNF-α. In another embodiment, the neurological disorder is selected from a neurodegenerative disease, which may be associated with neuroinflammation. In certain embodiments, the inflammatory neurodegenerative disorder is selected from the group consisting of multiple sclerosis, Parkinson's disease, Huntington's disease, amyotropic lateral sclerosis (ALS), amyloidosis and dementia. In one embodiment, the inflammatory neurodegenerative disorder is amyloidosis selected from the group consisting of Alzheimer's disease, frontotemporal dementia, and Lewy body dementia. In one embodiment, the neurological disorder is any disorder characterized by elevated TNF-α, and can include such disorders as stroke, depression, post-traumatic stress syndrome and traumatic brain injury.

Preferably, the dominant negative TNF-α inhibitor is a dominant negative TNF-α polypeptide, which more preferably comprises a variant sequence relative to wild-type TNF-α, and which may be PEGylated. Such variant sequence may comprise the amino acid substitutions A145R/I97T or V1M/R31C/C69V/Y87H/C101A/A145R. In a preferred embodiment, the TNF-α polypeptide inhibits soluble TNF-α but does not inhibit signaling by transmembrane TNF-α. In another preferred embodiment, the dominant negative TNF-α polypeptide is XPro1595.

Also provided herein are methods of preventing neuron death, inhibiting microglial cell activation, inhibiting demyelination, and/or promoting remyelination in a patient in need thereof, each method comprising peripherally administering a therapeutically effective amount of a dominant negative TNF-α inhibitor.

BRIEF DESCRIPTION OF THE DRAWINGS

FIG. 1A shows the nucleic acid sequence of human TNF-α (SEQ ID NO:1). An additional six histidine codons, located between the start codon and the first amino acid, are underlined.

FIG. 1B shows the amino acid sequence of human TNF-α (SEQ ID NO:2) with an additional 6 histidines (underlined) between the start codon and the first amino acid. Amino acids changed in exemplary TNF-α variants are shown in bold.

FIG. 2 shows the positions and amino acid changes in certain TNF-α variants.

Similar analysis of phosphorylated-inhibitor of NF-κB (p-IκB) and phosphorylated p65 NF-κB subunit (p-p65; arrowhead) protein levels in spinal cord extracts from naïve and Day 22 EAE mice from different treatment groups (XPro1595, n=4; etanercept, n=4; vehicle, n=3; naïve=5). (C) FLIP, vascular endothelial growth factor (VEGF) and CSF-1 receptor messenger RNA transcript levels in spinal cord extracts from EAE mice at peak and Day 39 post-immunization by semi-quantitative RT-polymerase chain reaction using β-actin for normalization.

Figure 7:
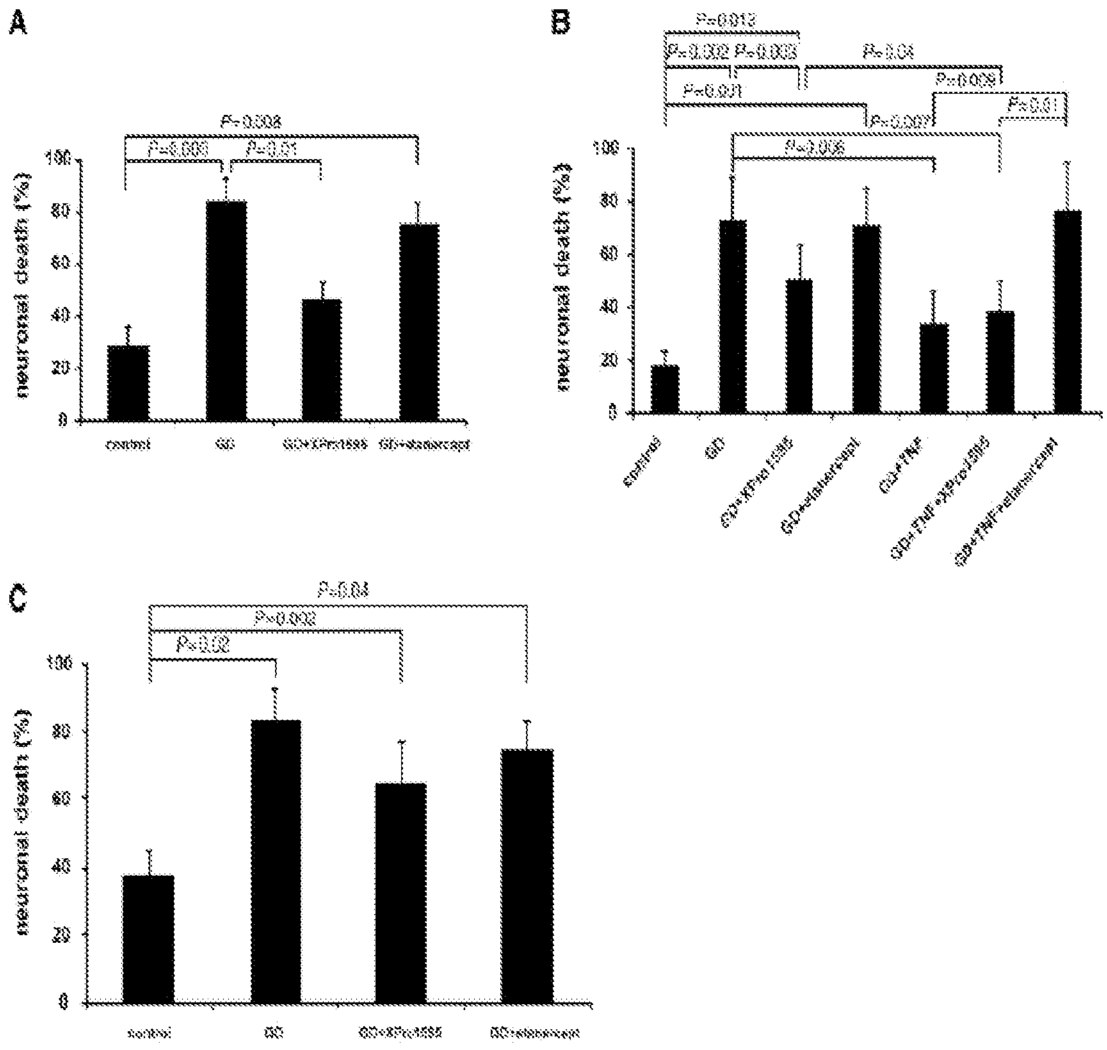

FIG. 7—Transmembrane TNF mediates neuroprotection in neuron-astrocyte co-cultures that is dependent on contact between the two cell types. (A) glucose deprivation-induced neuron death in astrocyte-neuron co-cultures that were incubated with XPro1595 (200 ng/ml), etanercept (100 ng/ml) or saline starting 4 h after the onset of glucose deprivation (GD). Neuron death is shown as the percentage of trypan blue (TB)-positive cells (dead) to total cell number in each experimental condition. (B) Glucose deprivation-induced neuron death in astrocyte-neuron co-cultures that have been pretreated for 24 h with human TNF (50 ng/ml) prior to glucose deprivation and incubated with XPro1595, etanercept or saline starting 4 h after the onset of glucose deprivation. (C) Glucose deprivation-induced neuron death in astrocyte-neuron co-cultures where astrocytes were separated from neurons by Transwells, treated with XPro1595, etanercept or saline starting 4 h after the onset of glucose deprivation.

Figure 8:
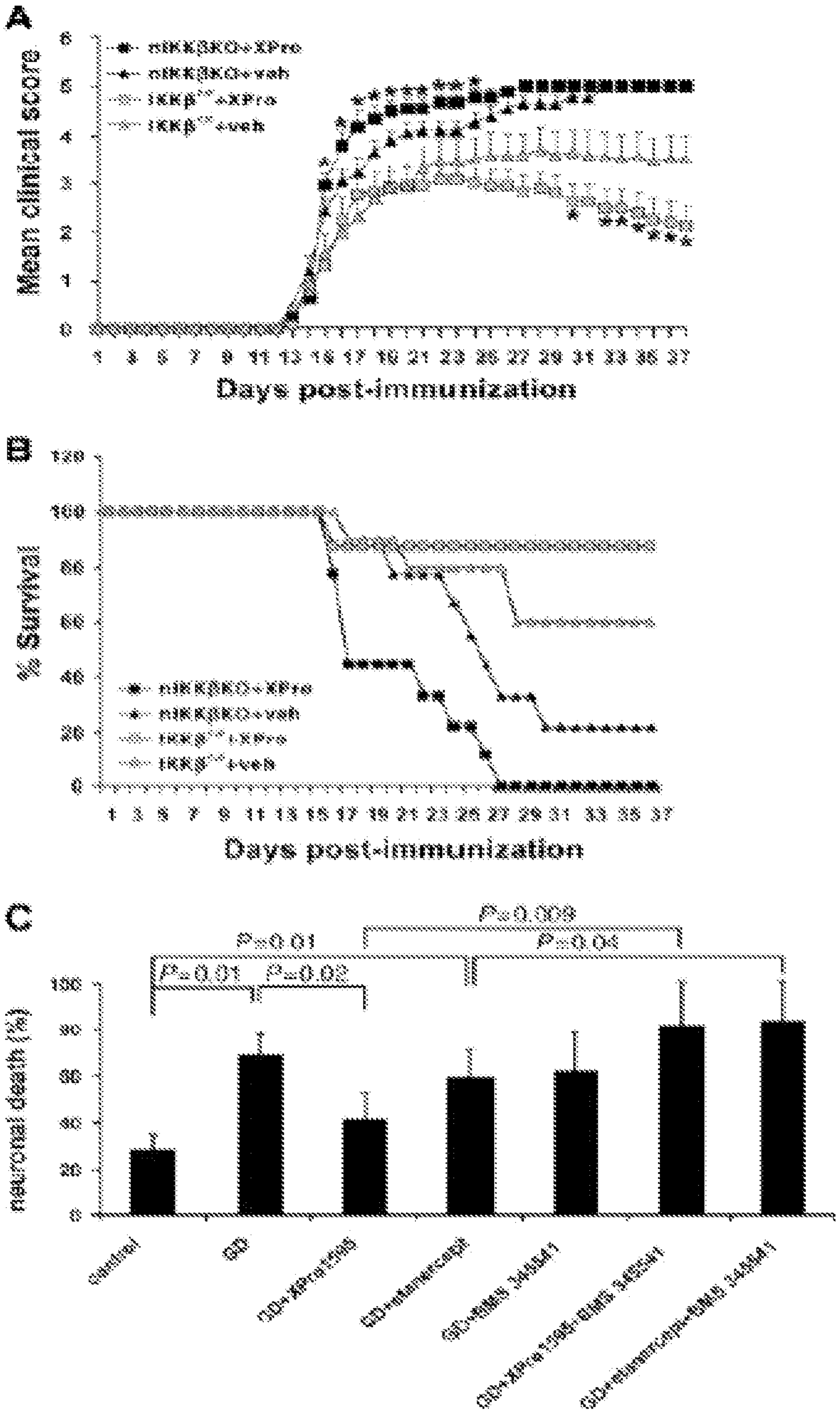

FIG. 8—Transmembrane TNF-mediated neuroprotection in vivo in EAE is dependent upon neuronal NF-κB signalling. (A) Clinical EAE scores (means±SEM) over time for nIKKβKO mice treated with XPro 1595 (filled square; n=9) or vehicle (filled triangle; n=10) and IKKβ$^{F/F}$ mice treated with XPro1595 (open square; n=9) or vehicle (open triangle; n=10). (B) Survival (Kaplan-Meier) curve showing viability of mice (groups described in A) during disease progression. (C) Neuron viability in astrocyte-neuron co-cultures that were pretreated for 2 h prior to glucose deprivation with the selective IKKβ inhibitor, BMS 34 5541 (25 μM) and then treated with XPro1595 (200 ng/ml) or etanercept (100 ng/ml) starting 4 h after glucose deprivation.

Figure 9:
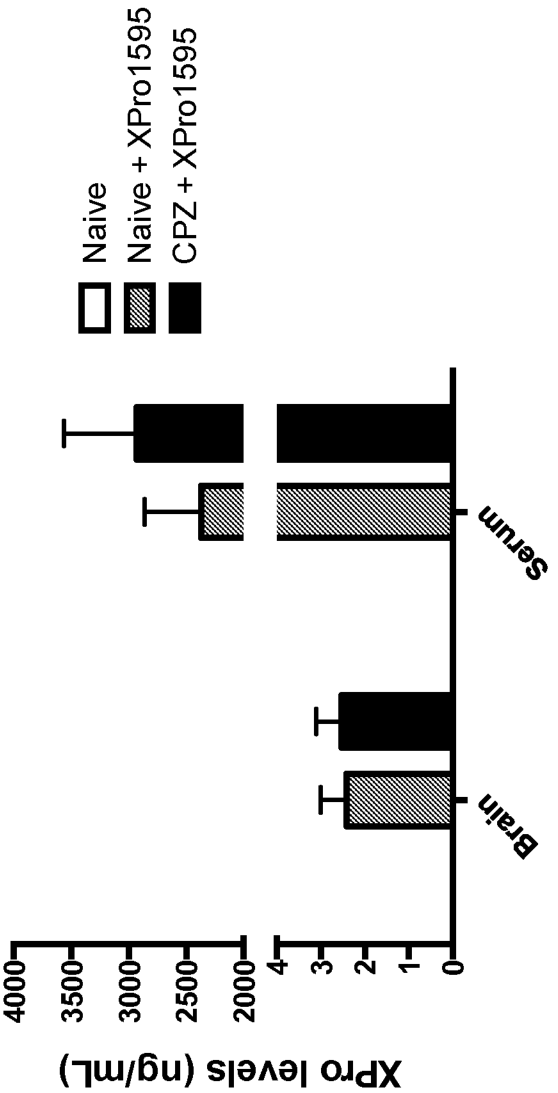

FIG. 9 XPro1595 crosses the blood brain barrier in both naïve and cuprizone-treated animals.

FIG. 10—Shows the amino acid sequence of human TNF-α (SEQ ID NO:3).

DETAILED DESCRIPTION

Disclosed herein is the finding that the inhibitors of TNF-α disclosed herein (e.g., dominant negative TNFα proteins) cross the blood brain barrier, allowing such inhibitors to be administered via a peripheral route, i.e., not intracranially and/or perispinally. Moreover, disclosed herein is the finding that while the disclosed inhibitors of TNF-α reduce inflammation in the brain, some such inhibitors may also (1) inhibit the signaling of soluble, but not membrane bound TNFα, (2) protect myelination of neurons and/or (3) promote remyelination of neurons.

Accordingly, the present invention addresses many of problems of prior art related to treatment of neurological diseases associated with elevated TNF-α, including but not limited to inflammatory neurodegenerative diseases. First, it allows for the first time a method of treating a neurological disorder following peripheral, as opposed to intracranial, administration of a therapeutic DN-TNF. It also allows for a treatment in which the inflammatory response in the brain is reduced, yet myelination of neurons is protected. In some embodiments remyelination of neurons is actually promoted following treatment with the inhibitors of TNF-α described herein. This is in stark contrast to commercially available TNF-α inhibitors, which promote neuron demyelination resulting in worsening of the disorders. Accordingly, the present invention provides a method of treating neurological disorders characterized by elevated TNF-α and/or neuroinflammation in which myelination of the neurons is protected and in some embodiments is improved. Accordingly, such inhibitors of TNF-α may be administered to a patient in need thereof, e.g., a patient with a neurological disorder, wherein said administration is via a peripheral, i.e., not intracranial, route.

Inhibitors of TNF-α

Preferred inhibitors of TNFα may be dominant negative TNFα proteins, referred to herein as "DNTNF-α," "DN-TNF-α proteins," "TNFα variants," "TNFα variant proteins," "variant TNF-α," "variant TNF-α," and the like. By "variant TNF-α" or "TNF-α proteins" is meant TNFα or TNF-α proteins that differ from the corresponding wild type protein by at least 1 amino acid. Thus, a variant of human TNF-α is compared to SEQ ID NO:1 (nucleic acid including codons for 6 histidines), SEQ ID NO:2 (amino acid including 6 N-terminal histidines) or SEQ ID NO:3 (amino acid without 6 N-terminal histidines). DN-TNF-α proteins are disclosed in detail in U.S. Pat. No. 7,446,174, which is incorporated herein in its entirety by reference. As used herein variant TNF-α or TNF-α proteins include TNF-α monomers, dimers or trimers. Included within the definition of "variant TNF-α" are competitive inhibitor TNF-α variants. While certain variants as described herein, one of skill in the art will understand that other variants may be made while retaining the function of inhibiting soluble but not transmembrane TNF-α.

Thus, the proteins of the invention are antagonists of wild type TNF-α. By "antagonists of wild type TNF-α" is meant that the variant TNF-α protein inhibits or significantly decreases at least one biological activity of wild-type TNF-α.

In a preferred embodiment the variant is antagonist of soluble TNF-α, but does not significantly antagonize transmembrane TNF-α, e.g., DN-TNF-α protein as disclosed herein inhibits signaling by soluble TNF-α, but not transmembrane TNF-α. By "inhibits the activity of TNF-α" and grammatical equivalents is meant at least a 10% reduction in wild-type, soluble TNF-α, more preferably at least a 50% reduction in wild-type, soluble TNF-α activity, and even more preferably, at least 90% reduction in wild-type, soluble TNF-α activity. Preferably there is an inhibition in wild-type soluble TNF-α activity in the absence of reduced signaling by transmembrane TNF-α. In a preferred embodiment, the activity of soluble TNF-α is inhibited while the activity of transmembrane TNF-α is substantially and preferably completely maintained.

The TNF proteins of the invention have modulated activity as compared to wild type proteins. In a preferred embodiment, variant TNF-α proteins exhibit decreased biological activity (e.g. antagonism) as compared to wild type TNF-α, including but not limited to, decreased binding to a receptor (p55, p75 or both), decreased activation and/or ultimately a loss of cytotoxic activity. By "cytotoxic activity" herein refers to the ability of a TNF-α variant to selectively kill or inhibit cells. Variant TNF-α proteins that exhibit less than 50% biological activity as compared to wild type are preferred. More preferred are variant TNF-α proteins that exhibit less than 25%, even more preferred are variant proteins that exhibit less than 15%, and most preferred are variant TNF-α proteins that exhibit less than 10% of a biological activity of wild-type TNF-α. Suitable assays include, but are not limited to, caspase assays, TNF-α cytotoxicity assays, DNA binding assays, transcription assays (using reporter constructs), size exclusion chromatography assays and radiolabeling/immuno-precipitation,), and stability assays (including the use of circular dichroism (CD) assays and equilibrium studies), according to methods know in the art.

In one embodiment, at least one property critical for binding affinity of the variant TNF-α proteins is altered when compared to the same property of wild type TNF-α and in particular, variant TNF-α proteins with altered receptor affinity are preferred. Particularly preferred are variant TNF-α with altered affinity toward oligomerization to wild type TNF-α. Thus, the invention provides variant TNF-α proteins with altered binding affinities such that the variant TNF-α proteins will preferentially oligomerize with wild type TNF-α, but do not substantially interact with wild type TNF receptors, i.e., p55, p75. "Preferentially" in this case means that given equal amounts of variant TNF-α monomers and wild type TNF-α monomers, at least 25% of the resulting trimers are mixed trimers of variant and wild type TNF-α, with at least about 50% being preferred, and at least about 80-90% being particularly preferred. In other words, it is preferable that the variant TNF-α proteins of the invention have greater affinity for wild type TNF-α protein as compared to wild type TNF-α proteins. By "do not substantially interact with TNF receptors" is meant that the variant TNF-α proteins will not be able to associate with either the p55 or p75 receptors to significantly activate the receptor and initiate the TNF signaling pathway(s). In a preferred embodiment, at least a 50% decrease in receptor activation is seen, with greater than 50%, 76%, 80-90% being preferred.

In some embodiments, the variants of the invention are antagonists of both soluble and transmembrane TNF-α. However, as described herein, preferred variant TNF-α proteins are antagonists of the activity of soluble TNF-α but do not substantially affect the activity of transmembrane TNF-α. Thus, a reduction of activity of the heterotrimers for soluble TNF-α is as outlined above, with reductions in biological activity of at least 10%, 25, 50, 75, 80, 90, 95, 99 or 100% all being preferred. However, some of the variants outlined herein comprise selective inhibition; that is, they inhibit soluble TNF-α activity but do not substantially inhibit transmembrane TNF-α. In these embodiments, it is preferred that at least 80%, 85, 90, 95, 98, 99 or 100% of the transmembrane TNF-α activity is maintained. This may also be expressed as a ratio; that is, selective inhibition can include a ratio of inhibition of soluble to transmembrane TNF-α. For example, variants that result in at least a 10:1 selective inhibition of soluble to transmembrane TNF-α activity are preferred, with 50:1, 100:1, 200:1, 500:1, 1000:1 or higher find particular use in the invention. Thus one embodiment utilizes variants, such as double mutants at positions 87/145 as outlined herein, that substantially inhibit or eliminate soluble TNF-α activity (for example by exchanging with homotrimeric wild-type to form heterotrimers that do not bind to TNF-α receptors or that bind but do not activate receptor signaling) but do not significantly affect (and preferably do not alter at all) transmembrane TNF-α activity. Without being bound by theory, the variants exhibiting such differential inhibition allow the decrease of inflammation without a corresponding loss in immune response, or when in the context of the appropriate cell, without a corresponding demyelination of neurons.

In one embodiment, the affected biological activity of the variants is the activation of receptor signaling by wild type TNF-α proteins. In a preferred embodiment, the variant TNF-α protein interacts with the wild type TNF-α protein such that the complex comprising the variant TNF-α and wild type TNF-α has reduced capacity to activate (as outlined above for "substantial inhibition"), and in preferred embodiments is incapable of activating, one or both of the TNF receptors, i.e. p55 TNF-R or p75 TNF-R. In a preferred embodiment, the variant TNF-α protein is a variant TNF-α protein that functions as an antagonist of wild type TNF-α. Preferably, the variant TNF-α protein preferentially interacts with wild type TNF-α to form mixed trimers with the wild type protein such that receptor binding does not significantly occur and/or TNF-α signaling is not initiated. By mixed trimers is meant that monomers of wild type and variant TNF-α proteins interact to form heterotrimeric TNF-α. Mixed trimers may comprise 1 variant TNF-α protein:2 wild type TNF-α proteins, 2 variant TNF-α proteins:1 wild type TNF-α protein. In some embodiments, trimers may be formed comprising only variant TNF-α proteins.

The variant TNF-α antagonist proteins of the invention are highly specific for TNF-α antagonism relative to TNF-beta antagonism. Additional characteristics include improved stability, pharmacokinetics, and high affinity for wild type TNF-α. Variants with higher affinity toward wild type TNF-α may be generated from variants exhibiting TNF-α antagonism as outlined above.

Similarly, variant TNF-α proteins, for example are experimentally tested and validated in in vivo and in in vitro assays. Suitable assays include, but are not limited to, activity assays and binding assays. For example, TNF-α activity assays, such as detecting apoptosis via caspase activity can be used to screen for TNF-α variants that are antagonists of wild type TNF-α. Other assays include using the Sytox green nucleic acid stain to detect TNF-induced cell permeability in an Actinomycin-D sensitized cell line. As this stain is excluded from live cells, but penetrates dying cells, this assay also can be used to detect TNF-α variants that are agonists of wild-type TNF-α. By "agonists of "wild type TNF-α" is meant that the variant TNF-α protein enhances the activation of receptor signaling by wild type TNF-α proteins. Generally, variant TNF-α proteins that function as agonists of wild type TNF-α are not preferred. However, in some embodiments, variant TNF-α proteins that function as agonists of wild type TNF-α protein are preferred. An example of an NF kappaB assay is presented in Example 7 of U.S. Pat. No. 7,446,174, which is expressly incorporated herein by reference.

In a preferred embodiment, binding affinities of variant TNF-α proteins as compared to wild type TNF-α proteins for naturally occurring TNF-α and TNF receptor proteins such as p55 and p75 are determined. Suitable assays include, but are not limited to, e.g., quantitative comparisons comparing kinetic and equilibrium binding constants, as are known in the art. Examples of binding assays are described in Example 6 of U.S. Pat. No. 7,446,174, which is expressly incorporated herein by reference.

In a preferred embodiment, the variant TNF-α protein has an amino acid sequence that differs from a wild type TNF-α sequence by at least 1 amino acid, with from 1, 2, 3, 4, 5, 6, 7, 8, 9 and 10 amino acids all contemplated, or higher. Expressed as a percentage, the variant TNF-α proteins of the invention preferably are greater than 90% identical to wild-type, with greater than 95, 97, 98 and 99% all being contemplated. Stated differently, based on the human TNF-α sequence of FIG. 1B (SEQ ID NO:2) excluding the N-terminal 6 histidines, as shown in FIG. 10 (SEQ ID NO:3), variant TNF-α proteins have at least about 1 residue that differs from the human TNF-α sequence, with at least about 2, 3, 4, 5, 6, 6 or 8 different residues. Preferred variant TNF-α proteins have 3 to 8 different residues.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

TNF-α proteins may be fused to, for example, to other therapeutic proteins or to other proteins such as Fc or serum albumin for therapeutic or pharmacokinetic purposes. In this embodiment, a TNF-α protein of the present invention is operably linked to a fusion partner. The fusion partner may be any moiety that provides an intended therapeutic or pharmacokinetic effect. Examples of fusion partners include but are not limited to Human Serum Albumin, a therapeutic agent, a cytotoxic or cytotoxic molecule, radionucleotide, and an Fc, etc. As used herein, an Fc fusion is synonymous with the terms "immunoadhesin", "Ig fusion", "Ig chimera", and "receptor globulin" as used in the prior art (Chamow et al., 1996, *Trends Biotechnol* 14:52-60; Ashkenazi et al., 1997, *Curr Opin Immunol* 9:195-200, both incorporated by reference). An Fc fusion combines the Fc region of an immunoglobulin with the target-binding region of a TNF-α protein, for example. See for example U.S. Pat. Nos. 5,766,883 and 5,876,969, both of which are incorporated by reference.

Figure 3:
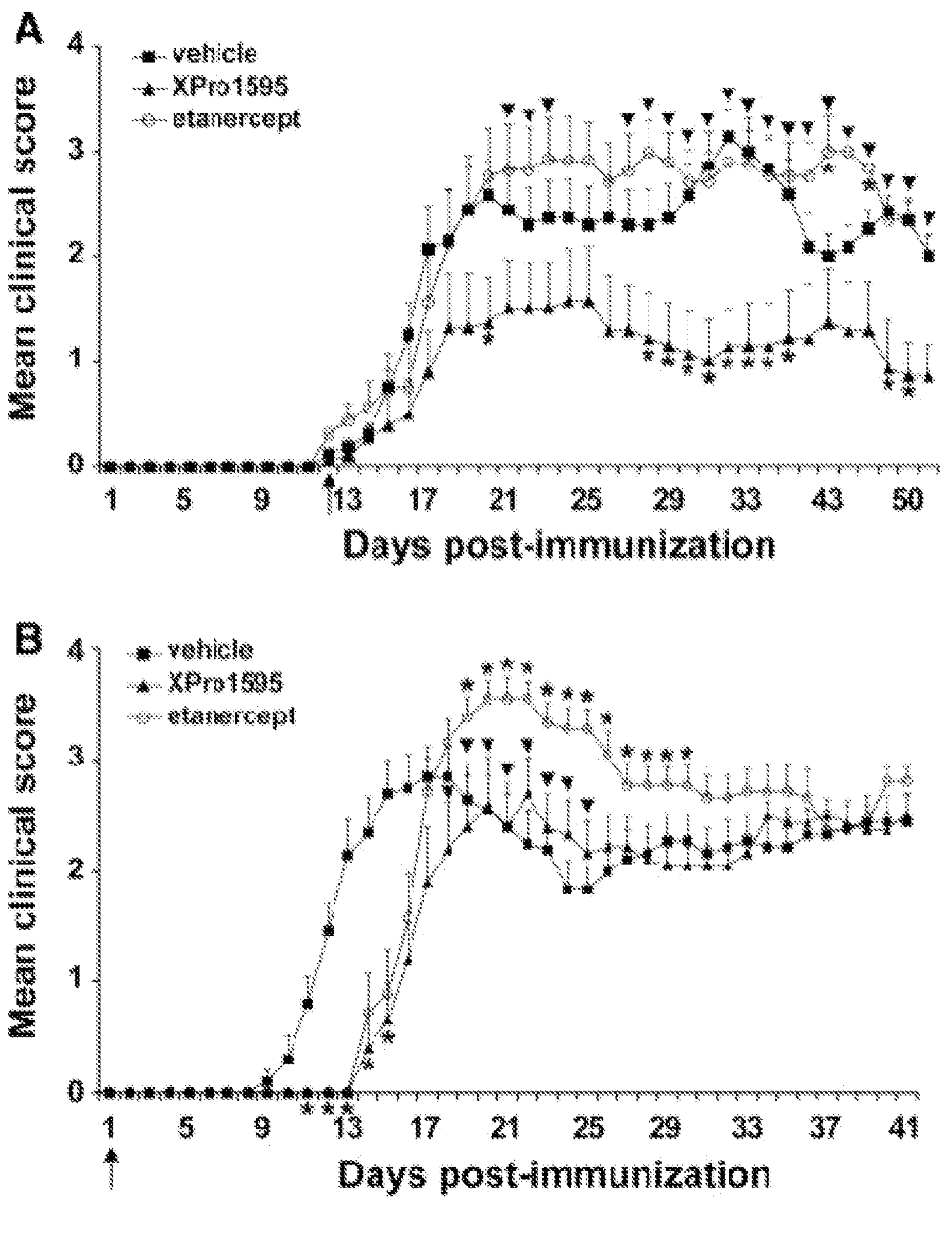
FIG. 3—EAE is ameliorated by the inhibition of soluble TNF, but not of soluble TNF and transmembrane TNF.

In a preferred embodiment, the variant TNF-α proteins comprise variant residues selected from the following positions 21, 23, 30, 31, 32, 33, 34, 35, 57, 65, 66, 67, 69, 75, 84, 86, 87, 91, 97, 101, 111, 112, 115, 140, 143, 144, 145, 146, and 147. Preferred amino acids for each position, including the human TNF-α residues, are shown in FIG. 3. Thus, for example, at position 143, preferred amino acids are Glu, Asn, Gln, Ser, Arg, and Lys; etc. Preferred changes include: V1M, Q21C, Q21 R, E23C, R31C, N34E, V91E, Q21R, N30D, R31C, R31I, R31D, R31E, R32D, R32E, R32S, A33E, N34E, N34V, A35S, D45C, L57F, L57W, L57Y, K65D, K65E, K651, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R. These may be done either individually or in combination, with any combination being possible. However, as outlined herein, preferred embodiments utilize at least 1 to 8, and preferably more, positions in each variant TNF-α protein.

In an additional aspect, the invention provides TNF-α variants selected from the group consisting of XENP268 XENP344, XENP345, XENP346, XENP550, XENP551, XENP557, XENP1593, XENP1594, and XENP1595 as outlined in Example 3 OF U.S. Pat. No. 7,662,367, which is incorporated herein by reference.

In an additional aspect, the invention provides methods of forming a TNF-α heterotrimer in vivo in a mammal comprising administering to the mammal a variant TNF-α molecule as compared to the corresponding wild-type mammalian TNF-α, wherein said TNF-α variant is substantially free of agonistic activity.

In an additional aspect, the invention provides methods of screening for selective inhibitors comprising contacting a candidate agent with a soluble TNF-α protein and assaying for TNF-α biological activity; contacting a candidate agent with a transmembrane TNF-α protein and assaying for TNF-α biological activity, and determining whether the agent is a selective inhibitor. The agent may be a protein (including peptides and antibodies, as described herein) or small molecules.

In a further aspect, the invention provides variant TNF-α proteins that interact with the wild type TNF-α to form mixed trimers incapable of activating receptor signaling. Preferably, variant TNF-α proteins with 1, 2, 3, 4, 5, 6 and 7 amino acid changes are used as compared to wild type TNF-α protein. In a preferred embodiment, these changes are selected from positions 1, 21, 23, 30, 31, 32, 33, 34, 35, 57, 65, 66, 67, 69, 75, 84, 86, 87, 91, 97, 101, 111, 112, 115, 140, 143, 144, 145, 146 and 147. In an additional aspect, the non-naturally occurring variant TNF-α proteins have substitutions selected from the group of substitutions consisting of V1M, Q21C, Q21R, E23C, N34E, V91E, Q21R, N30D, R31C, R311, R31D, R31E, R32D, R32E, R32S, A33E, N34E, N34V, A35S, D45C, L57F, L57W, L57Y, K65D, K65E, K651, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R.

In another preferred embodiment, substitutions may be made either individually or in combination, with any combination being possible. Preferred embodiments utilize at least one, and preferably more, positions in each variant TNF-α protein. For example, substitutions at positions 31, 57, 69, 75, 86, 87, 97, 101, 115, 143, 145, and 146 may be combined to form double variants. In addition triple, quadruple, quintuple and the like, point variants may be generated.

In one aspect the invention provides TNF-α variants comprising the amino acid substitutions A145R/I97T. In one aspect, the invention provides TNF-α variants comprising the amino acid substitutions V1M, R31C, C69V, Y87H, C101A, and A145R. In a preferred embodiment, this variant is PEGylated.

In a preferred embodiment the variant is XPro1595, a PEGylated protein comprising V1M, R31C, C69V, Y87H, C101A, and A145R mutations relative to the wild type human sequence.

For purposes of the present invention, the areas of the wild type or naturally occurring TNF-α molecule to be modified are selected from the group consisting of the Large Domain (also known as II), Small Domain (also known as I), the DE loop, and the trimer interface. The Large Domain, the Small Domain and the DE loop are the receptor interaction domains. The modifications may be made solely in one of these areas or in any combination of these areas. The Large Domain preferred positions to be varied include: 21, 30, 31, 32, 33, 35, 65, 66, 67, 111, 112, 115, 140, 143, 144, 145, 146 and/or 147. For the Small Domain, the preferred positions to be modified are 75 and/or 97. For the DE Loop, the preferred position modifications are 84, 86, 87 and/or 91. The Trimer Interface has preferred double variants including positions 34 and 91 as well as at position 57. In a preferred embodiment, substitutions at multiple receptor interaction and/or trimerization domains may be combined. Examples include, but are not limited to, simultaneous substitution of amino acids at the large and small domains (e.g. A145R and I97T), large domain and DE loop (A145R and Y87H), and large domain and trimerization domain (A145R and L57F). Additional examples include any and all combinations, e.g., I97T and Y87H (small domain and DE loop). More specifically, theses variants may be in the form of single point variants, for example K112D, Y115K, Y115I, Y115T, A145E or A145R. These single point variants may be combined, for example, Y115I and A145E, or Y115I and A145R, or Y115T and A145R or Y115I and A145E; or any other combination.

Preferred double point variant positions include 57, 75, 86, 87, 97, 115, 143, 145, and 146; in any combination. In addition, double point variants may be generated including L57F and one of Y115I, Y115Q, Y115T, D143K, D143R, D143E, A145E, A145R, E146K or E146R. Other preferred double variants are Y115Q and at least one of D143N, D143Q, A145K, A145R, or E146K; Y115M and at least one of D143N, D143Q, A145K, A145R or E146K; and L57F and at least one of A145E or 146R; K65D and either D143K or D143R, K65E and either D143K or D143R, Y115Q and any of L75Q, L57W, L57Y, L57F, I97R, I97T, S86Q, D143N, E146K, A145R and I97T, A145R and either Y87R or Y87H; N34E and V91E; L75E and Y115Q; L75Q and Y115Q; L75E and A145R; and L75Q and A145R.

Further, triple point variants may be generated. Preferred positions include 34, 75, 87, 91, 115, 143, 145 and 146. Examples of triple point variants include V91 E, N34E and one of Y115I, Y115T, D143K, D143R, A145R, A145E E146K, and E146R. Other triple point variants include L75E and Y87H and at least one of Y115Q, A145R, Also, L75K, Y87H and Y115Q. More preferred are the triple point variants V91E, N34E and either A145R or A145E.

Variant TNF-α proteins may also be identified as being encoded by variant TNF-α nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred. In a preferred embodiment, a variant TNF-α nucleic acid encodes a variant TNF-α protein. As will be appreciated by those in the art, due to the degeneracy of the genetic code, an extremely large number of nucleic acids may be made, all of which encode the variant TNF-α proteins of the present invention. Thus, having identified a particular amino acid sequence, those skilled in the art could make any number of different nucleic acids, by simply modifying the sequence of one or more codons in a way which does not change the amino acid sequence of the variant TNF-α.

In one embodiment, the nucleic acid homology is determined through hybridization studies. Thus, for example, nucleic acids which hybridize under high stringency to the nucleic acid sequence shown in FIG. 1A (SEQ ID NO:1) or its complement and encode a variant TNF-α protein is considered a variant TNF-α gene. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993), incorporated by reference. Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra. In addition, nucleic acid variants encode TNF-α protein variants comprising the amino acid substitutions described herein. In one embodiment, the TNF-α variant encodes a polypeptide variant comprising the amino acid substitutions A145R/197T. In one aspect, the nucleic acid variant encodes a polypeptide comprising the amino acid substitutions V1M, R31C, C69V, Y87H, C101A, and A145R, or any 1, 2, 3, 4 or 5 of these variant amino acids.

The variant TNF-α proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half-life of such molecules in physiological environments. The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1A (SEQ ID NO:1) also includes the complement of the sequence. By the term "recombinant nucleic acid" is meant nucleic acid, originally formed in vitro, in general, by the manipulation of nucleic acid by endonucleases, in a form not normally found in nature. Thus an isolated variant TNF-α nucleic acid, in a linear form, or an expression vector formed in vitro by ligating DNA molecules that are not normally joined, are both considered recombinant for the purposes of this invention.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild-type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a variant TNF-α protein from one organism in a different organism or host cell. Alternatively, the protein may be made at a significantly higher concentration than is normally seen, through the use of a inducible promoter or high expression promoter, such that the protein is made at increased concentration levels. Furthermore, all of the variant TNF-α proteins outlined herein are in a form not normally found in nature, as they contain amino acid substitutions, insertions and deletions, with substitutions being preferred, as discussed below.

Also included within the definition of variant TNF-α proteins of the present invention are amino acid sequence variants of the variant TNF-α sequences outlined herein and shown in the Figures. That is, the variant TNF-α proteins may contain additional variable positions as compared to human TNF-α. These variants fall into one or more of three classes: substitutional, insertional or deletional variants.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Using the nucleic acids of the present invention, which encode a variant TNF-α protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant TNF-α protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the variant TNF-α protein, a replacement of the naturally occurring secretory leader sequence is desired. In this embodiment, an unrelated secretory leader sequence is operably linked to a variant TNF-α encoding nucleic acid leading to increased protein secretion. Thus, any secretory leader sequence resulting in enhanced secretion of the variant TNF-α protein, when compared to the secretion of TNF-α and its secretory sequence, is desired. Suitable secretory leader sequences that lead to the secretion of a protein are known in the art. In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences that flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used. A preferred expression vector system is a retroviral vector system such as is generally described in PCT/US97/01019 and PCT/US97/01048, both of which are hereby incorporated by reference. In a preferred embodiment, the expression vector comprises the components described above and a gene encoding a variant TNF-α protein. As will be appreciated by those in the art, all combinations are possible and accordingly, as used herein, the combination of components, comprised by one or more vectors, which may be retroviral or not, is referred to herein as a "vector composition".

A number of viral based vectors have been used for gene delivery. See for example U.S. Pat. No. 5,576,201, which is expressly incorporated herein by reference. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector, which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors. Retroviral vectors can be constructed using techniques well known in the art. See, e.g., U.S. Pat. No. 5,219,740; Mann et al. (1983) Cell 33:153-159.

Adenovirus based systems have been developed for gene delivery and are suitable for delivery according to the methods described herein. Human adenoviruses are double-stranded DNA viruses that enter cells by receptor-mediated endocytosis. These viruses are particularly well suited for gene transfer because they are easy to grow and manipulate and they exhibit a broad host range in vivo and in vitro.

Adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low level morbidity and are not associated with human malignancies. Accordingly, adenovirus vectors have been developed which make use of these advantages. For a description of adenovirus vectors and their uses see, e.g., Haj-Ahmad and Graham (1986) *J. Virol.* 57:267-274; Bett et al. (1993) *J. Virol.* 67:5911-5921; Mittereder et al. (1994) *Human Gene Therapy* 5:717-729; Seth et al. (1994) *J. Virol.* 68:933-940; Barr et al. (1994) *Gene Therapy* 1:51-58; Berkner, K. L. (1988) BioTechniques 6:616-629; Rich et al. (1993) *Human Gene Therapy* 4:461-476.

In a preferred embodiment, the viral vectors used in the subject methods are AAV vectors. By an "AAV vector" is meant a vector derived from an adeno-associated virus serotype, including without limitation, AAV-1, AAV-2, AAV-3, AAV-4, AAV-5, AAVX7, etc. Typical AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. An AAV vector includes at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. For more on various AAV serotypes, see for example Cearley et al., *Molecular Therapy,* 16:1710-1718, 2008, which is expressly incorporated herein in its entirety by reference.

AAV expression vectors may be constructed using known techniques to provide as operatively linked components in the direction of transcription, control elements including a transcriptional initiation region, the DNA of interest and a transcriptional termination region. The control elements are selected to be functional in a thalamic and/or cortical neuron. Additional control elements may be included. The resulting construct, which contains the operatively linked components is bounded (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) *Human Gene Therapy* 5:793-801; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

Suitable DNA molecules for use in AAV vectors will include, for example, a gene that encodes a protein that is defective or missing from a recipient subject or a gene that encodes a protein having a desired biological or therapeutic effect (e.g., an enzyme, or a neurotrophic factor). The artisan of reasonable skill will be able to determine which factor is appropriate based on the neurological disorder being treated.

The selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

Once made, the TNF-α protein may be covalently modified. For instance, a preferred type of covalent modification of variant TNF-α comprises linking the variant TNF-α polypeptide to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689; 4,301,144; 4,670,417; 4,791,192 or 4,179,337, incorporated by reference. These nonproteinaceous polymers may also be used to enhance the variant TNF-α's ability to disrupt receptor binding, and/or in vivo stability. In another preferred embodiment, cysteines are designed into variant or wild type TNF-α in order to incorporate (a) labeling sites for characterization and (b) incorporate PEGylation sites. For example, labels that may be used are well known in the art and include but are not limited to biotin, tag and fluorescent labels (e.g. fluorescein). These labels may be used in various assays as are also well known in the art to achieve characterization. A variety of coupling chemistries may be used to achieve PEGylation, as is well known in the art. Examples include but are not limited to, the technologies of Shearwater and Enzon, which allow modification at primary amines, including but not limited to, lysine groups and the N-terminus See, Kinstler et al, Advanced Drug Deliveries Reviews, 54, 477-485 (2002) and M J Roberts et al, Advanced Drug Delivery Reviews, 54, 459-476 (2002), both hereby incorporated by reference.

In one preferred embodiment, the optimal chemical modification sites are 21, 23, 31 and 45, taken alone or in any combination. In an even more preferred embodiment, a TNF-α variant of the present invention includes the R31C mutation.

In a preferred embodiment, the variant TNF-α protein is purified or isolated after expression. Variant TNF-α proteins may be isolated or purified in a variety of ways known to those skilled in the art depending on what other components are present in the sample.

Neurological Disorders

As disclosed herein, when administered peripherally, DN-TNF-α proteins may reduce inflammation in the brain, and thus, may be used to treat neurological disorders, particularly those characterized by elevated TNF-α. In one embodiment the DN-TNF-α molecules disclosed herein find use in treating neurological disorders, e.g., by reducing inflammation in the brain, protecting myelination of neurons and/or promoting remyelination of neurons. Accordingly, neurological disorders particularly amenable to the methods disclosed herein include art-recognized inflammatory neurodegenerative diseases, which may result in the destruction of myelin or may include other neurological disorders not necessarily characterized by myelin destruction but are characterized by elevated levels of TNF-α.

In one embodiment, neurodegenerative diseases are a group of diseases typified by deterioration of neurons and/or their myelin sheath. This destruction of neurons eventually leads to dysfunction and disabilities. Often times inflammation, thought to be mediated by microglial cells, is found to be a component of neurodegenerative diseases and adds to the pathogenesis of the neurodegeneration. Collectively, these diseases comprise the art-recognized inflammatory neurodegenerative diseases. Neuroinflammation may occur years prior to any considerable loss of neurons in some neurodegenerative disorders. For example, 70% of dopaminergic neurons are lost from the substantia nigra before patients begin to manifest the clinical signs of Parkinson's disease, see, e.g., Factor and Weiner (2008) Parkinson's Disease: Diagnosis and Clinical Management. Many different types of immune cells, including macrophages, neutrophils, T cells, astrocytes, and microglia, can contributed to the pathology of immune-related diseases, like Multiple Sclerosis (M.S.), Parkinson's disease, Huntington's disease, dementia (including but not exclusively diseases like Alzheimer's disease, frontotemporal dementia, trauma related dementia (punch drunk), HIV-associated and Lewy Body dementia), amyotrophic lateral sclerosis (ALS), prion diseases, etc. More specifically, in MS the injury to myelin is mediated by an inflammatory response and M.S. Pathogenesis is exacerbated when leukocytes infiltrate the CNS.

Accordingly, inflammatory neurodegenerative diseases include but are not limited to: multiple sclerosis (MS), Parkinson's disease, amyloidosis (e.g., Alzheimer's disease), amyotrophic lateral sclerosis (ALS), HIV-associated dementia, stroke/cerebral ischemia, head trauma, spinal cord injury, Huntington's disease, migraine, cerebral amyloid angiopathy, AIDS, age-related cognitive decline; mild cognitive impairment and prion diseases in a mammal, and preferably in a human.

Multiple sclerosis (MS) is a chronic inflammatory neurodegenerative disease of the central nervous system (CNS) that affects approximately 1,100,000 people all over the world, in particular affects young adults. MS is characterized pathologically by demyelination of neural tissue, which results clinically in one of many forms of the disease, ranging from benign to chronic-progressive patterns of the disease state. More specifically, five main forms of multiple sclerosis have been described: 1) benign multiple sclerosis; 2) relapsing-remitting multiple sclerosis (RRMS); 3) secondary progressive multiple sclerosis (SPMS); 4) primary progressive multiple sclerosis (PPMS); and 5) progressive-relapsing multiple sclerosis (PRMS). Chronic progressive multiple sclerosis is a term used to collectively refer to SPMS, PPMS, and PRMS. The relapsing forms of multiple sclerosis are SPMS with superimposed relapses, RRMS and PRMS.

Throughout the course of the disease there is a progressive destruction of the myelin sheath surrounding axons. Since intact myelin is essential in the preservation of axonal integrity systematic destruction eventually leads, clinically, to various neurological dysfunctions including numbness and pain, problems with coordination and balance, blindness, and general cognitive impairment.

Parkinson's disease, another inflammatory neurodegenerative disease, is characterized by movement disorders, including muscle rigidity and slow physical movements.

Amyloidosis develops when certain proteins have altered structure and tend to bind to each building up in particular tissue and blocking the normal tissue functioning. These altered structured proteins are called amyloids. Often amyloidoses is split into two categories: primary or secondary. Primary amyloidoses occur from an illness with improper immune cell function. Secondary amyloidoses usually arise from a complication of some other chronic infectious or inflammatory diseases. Examples of such include Alzheimer's disease and rheumatoid arthritis. The underlying problem in secondary amyloidosis is inflammation.

Alzheimer's disease is another type of inflammatory neurodegenerative disease. It is exemplified by the increasing impairment of learning and memory, although the disease may manifest itself in other ways indicating altered cognitive ability. Throughout the disease the progressive loss of neurons and synapses in the cerebral cortex leads to gross atrophy of the neural tissue. Although the cause of Alzheimer's is unknown, many believe that inflammation plays an important role and clinical studies have shown that inflammation considerably contributes to the pathogenesis of the disease.

Amyotrophic lateral sclerosis is another debilitating neurological disorder. In ALS a link between inflammation and the disease has been suggested.

In one embodiment, the neurological disorder is any disorder characterized by elevated TNF-α, and can include disorders such as stroke, depression, post-traumatic stress syndrome and traumatic brain injury.

Treatment Methods

The terms "treatment", "treating", and the like, as used herein include amelioration or elimination of a disease or condition once it has been established or alleviation of the characteristic symptoms of such disease or condition. A method as disclosed herein may also be used to, depending on the condition of the patient, prevent the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement. In one embodiment, the method disclosed herein prevents the destruction of myelin after administration of a DN-TNF-α protein.

In one embodiment, a DN-TNFα protein as described herein is administered peripherally to a patient in need thereof to reduce neuroinflammation and/or prevent additional destruction of myelin. In another embodiment, a DN-TNFα protein as described herein is administered peripherally to a patient in need thereof to promote remyelination of neurons. In another embodiment, peripheral administration of a DN-TNFα protein as described herein results in reduced inflammation in the brain.

An inhibitor of TNF-α may be peripherally administered to a patient before 30%, more preferably before 25%, and most preferably before 20% of the patient's myelin and/or function is destroyed. In a preferred embodiment, the inhibitor of TNF-α may be peripherally administered to a patient when at least 85%, and more preferably at least 90%,or most preferably at least 95%-100% of the patient's myelin and/or function remains. In another embodiment, peripheral administration of an inhibitor of TNF-α as described herein may restore at least 25% or 30% or 40% or 50% or 60% or 70% or 80-% or 90%, or more of the total amount of demyelination prior to administration.

In one embodiment, the treatment method includes administering a DN-TNF molecule as described herein to a patient suffering from neurodegenerative disease. Once treated, the patient may be monitored for improvements by measuring a number of biomarkers, including activation of microglial cells or lipopolysaccharide (LPS) as is known in the art. In addition, levels of C-reactive protein may be measured according to methods known in the art as an indication of inflammation. As these markers have been found to be elevated in patients suffering from inflammatory neurodegenerative disease, following treatment with a DN-TNF as described herein microglial activation, LPS or C-reactive protein levels are reduced as compared to levels prior to treatment.

In one embodiment, the methods comprise peripheral administration of the DN-TNF for treatment of the neurological disorder, such as inflammatory neurodegenerative disease. By peripheral administration is meant administration other than directed administration to the brain, e.g. delivery by injection or other delivery to the patient in a peripheral manner not by directed administration to the brain. Without being bound by theory it is believed that despite the presence of the blood brain barrier, peripheral administration of the DN-TNF to a patient afflicted with or prone to being afflicted with an inflammatory neurodegenerative disease, will result in therapeutically effective doses of the DN-TNF in the brain. In one embodiment, the DN-TNF-α crosses the blood brain barrier and effectively treats the neurological disorder as described herein. In some embodiments, the DN-TNF crosses a competent blood brain barrier, e.g. one not characterized as "leaky", such as may exist under some conditions of neuroinflammation. As necessary, this can be assayed by monitoring biomarkers for the inflammatory neurodegenerative disease or direct detection of DN-TNF in the brain, using antibodies or other assays as are known in the art.

Alternatively, activation of microglial cells or elevation of lipopolysaccharide levels may be monitored in a putative patient prior to administration of a DN-TNF molecule as described herein. When either of these markers is elevated as compared to a healthy control, the patient may be in need of treatment with a DN-TNF as described herein, such as XPro1595.

In an alternative embodiment the method comprises topical administration of DN-TNF variants as described herein to the skin for treatment of autoimmune skin disorders, including psoriasis. In this embodiment the DN-TNF may be formulated as a lotion or cream as described herein.

Combination Treatments:

Treatments that currently are available for MS include glatiramer acetate, interferonβ, natalizumab, and mitoxanthrone. In general, these drugs suppress the immune system in a nonspecific fashion and only marginally limit the overall progression of disease. (Lubetzki et al. (2005), *Curr. Opin. Neural.* 18:237-244). Thus, there exists a need for developing therapeutic strategies to better treat MS. As described herein, DN-TNFs that inhibit soluble but not transmembrane TNF-α find use in treating MS. These molecules find particular use when combined with currently available MS therapies as known in the art and as described herein. For instance, DN-TNFs, such as XPro1595 may be combined in a therapeutic regimen with glatiramer acetate, interferon-β, natalizumab, and mitoxanthron or other molecules, such as bardoxolone methyl or variants thereof.

As another example, in the treatment of Alzheimer's Disease (AD), a DN-TNF protein may be administered to an individual in combination therapy with one or more additional therapeutic agents for the treatment of AD. Suitable additional therapeutic agents include, but are not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept is generally administered at 50 mg orally per day for 6 weeks, and, if well tolerated by the individual, at 10 mg per day thereafter.

In one embodiment, treatment of the DN-TNF in a therapeutic regimen in combination with the co-therapies as described herein results in synergistic efficacy as compared to either of the treatments alone. By "synergistic" is meant that efficacy is more than the result of additive efficacy of the two treatments alone.

In one embodiment treatment of the DN-TNF in a therapeutic regimen includes the combination of steroidal anti-inflammatory molecules, such as but not limited to dexamethasone and the like or non-steroidal anti-inflammatory molecules.

In addition, the DN-TNF may be formulated alone as a topical therapy or used in combination with or treated in a regimen with corticosteroids for treatment of autoimmune skin disorders such as psoriasis, eczema and burns (including sunburn). For instance, bath solutions and moisturizers, mineral oil and petroleum jelly which may help soothe affected skin and reduce the dryness which accompanies the build-up of skin on psoriatic plaques may be used formulated with or in a therapeutic regimen with DN-TNF as described herein. In addition, medicated creams and ointments applied directly to psoriatic plaques can help reduce inflammation, remove built-up scale, reduce skin turn over, and clear affected skin of plaques. Ointment and creams containing coal, tar, dithranol (anthralin), corticosteroids like desoximetasone (Topicort), fluocinonide, vitamin D3 analogs (for oexample, calcipotriol), and retinoids find use when combined with DN-TNF for topical application to the skin for treatment of autoimmune skin disorders.

Formulations

Depending upon the manner of introduction, the pharmaceutical composition may be formulated in a variety of ways. The concentration of the therapeutically active variant TNF-α protein in the formulation may vary from about 0.1 to 100 weight %. In another preferred embodiment, the concentration of the variant TNF-α protein is in the range of 0.003 to 1.0 molar, with dosages from 0.03, 0.05, 0.1, 0.2, and 0.3 millimoles per kilogram of body weight being preferred.

The pharmaceutical compositions of the present invention comprise a variant TNF-α protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, hereby incorporated by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be.

In one embodiment provided herein, antibodies, including but not limited to monoclonal and polyclonal antibodies, are raised against variant TNF-α proteins using methods known in the art. In a preferred embodiment, these anti-variant TNF-α antibodies are used for immunotherapy. Thus, methods of immunotherapy are provided. By "immunotherapy" is meant treatment of an TNF-α related disorders with an antibody raised against a variant TNF-α protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a variant TNF-α protein antigen to which antibodies are raised. As appreciated by one of ordinary skill in the art, the variant TNF-α protein antigen may be provided by injecting a variant TNF-α polypeptide against which antibodies are desired to be raised into a recipient, or contacting the recipient with a variant TNF-α protein encoding nucleic acid, capable of expressing the variant TNF-α protein antigen, under conditions for expression of the variant TNF-α protein antigen.

In another preferred embodiment, a therapeutic compound is conjugated to an antibody, preferably an anti-variant TNF-α protein antibody. The therapeutic compound may be a cytotoxic agent. In this method, targeting the cytotoxic agent to tumor tissue or cells, results in a reduction in the number of afflicted cells, thereby reducing symptoms associated with cancer, and variant TNF-α protein related disorders. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, variant TNF-α proteins are administered as therapeutic agents, and can be formulated as outlined above. Similarly, variant TNF-α genes (including both the full-length sequence, partial sequences, or regulatory sequences of the variant TNF-α coding regions) may be administered in gene therapy applications, as is known in the art. These variant TNF-α genes can include antisense applications, either as gene therapy (i.e. for incorporation into the genome) or as antisense compositions, as will be appreciated by those in the art.

In a preferred embodiment, the nucleic acid encoding the variant TNF-α proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. U.S.A.* 83:4143-4146 (1986), incorporated by reference). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11:205-210 (1993), incorporated by reference). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262:4429-4432 (1987); and Wagner et al., *Proc. Natl. Acad. Sci. U.S.A.* 87:3410-3414 (1990), both incorporated by reference. For review of gene marking and gene therapy protocols see Anderson et al., *Science* 256:808-813 (1992), incorporated by reference.

In a preferred embodiment, variant TNF-α genes are administered as DNA vaccines, either single genes or combinations of variant TNF-α genes. Naked DNA vaccines are generally known in the art. Brower, *Nature Biotechnology,* 16:1304-1305 (1998). Methods for the use of genes as DNA vaccines are well known to one of ordinary skill in the art, and include placing a variant TNF-α gene or portion of a variant TNF-α gene under the control of a promoter for expression in a patient in need of treatment. The variant TNF-α gene used for DNA vaccines can encode full-length variant TNF-α proteins, but more preferably encodes portions of the variant TNF-α proteins including peptides derived from the variant TNF-α protein. In a preferred embodiment a patient is immunized with a DNA vaccine comprising a plurality of nucleotide sequences derived from a variant TNF-α gene. Similarly, it is possible to immunize a patient with a plurality of variant TNF-α genes or portions thereof as defined herein. Without being bound by theory, expression of the polypeptide encoded by the DNA vaccine, cytotoxic T-cells, helper T-cells and antibodies are induced, which recognize and destroy or eliminate cells expressing TNF-α proteins.

In a preferred embodiment, the DNA vaccines include a gene encoding an adjuvant molecule with the DNA vaccine. Such adjuvant molecules include cytokines that increase the immunogenic response to the variant TNF-α polypeptide encoded by the DNA vaccine. Additional or alternative adjuvants are known to those of ordinary skill in the art and find use in the invention.

Pharmaceutical compositions are contemplated wherein a TNF-α variant of the present invention and one or more therapeutically active agents are formulated. Formulations of the present invention are prepared for storage by mixing TNF-α variant having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Lyophilization is well known in the art, see, e.g., U.S. Pat. No. 5,215,743, incorporated entirely by reference. Acceptable carriers, excipients, or stabilizers are nontoxic to recipients at the dosages and concentrations employed, and include buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN®, PLURONICS® or polyethylene glycol (PEG). In a preferred embodiment, the pharmaceutical composition that comprises the TNF-α variant of the present invention may be in a water-soluble form. The TNF-α variant may be present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferrably sterile. This is readily accomplished by filtration through sterile filtration membranes or other methods.

Controlled Release

In addition, any of a number of delivery systems are known in the art and may be used to administer TNF-α variants of the present invention. Examples include, but are not limited to, encapsulation in liposomes, microparticles, microspheres (e.g. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-gutamate, ethylene-vinyl acetate, lactic acid-glycolic acid copolymers such as the LUPRON DEPOT®, and poly-D-(−)-3-hydroxyburyric acid. It is also possible to administer a nucleic acid encoding the TNF-α of the current invention, for example by retroviral infection, direct injection, or coating with lipids, cell surface receptors, or other transfection agents. In all cases, controlled release systems may be used to release the TNF-α at or close to the desired location of action.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, incorporated entirely by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be. The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, incorporated entirely by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be.

Dosage forms for the topical or transdermal administration of a DN-TNF-protein disclosed herein include powders, sprays, ointments, pastes, creams, lotions, gels, solutions, patches and inhalants. The DN-TNF-protein may be mixed under sterile conditions with a pharmaceutically-acceptable carrier, and with any preservatives, buffers, or propellants which may be required. Powders and sprays can contain, in addition to the DN-TNF-protein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Methods of Administration

The administration of the variant TNF-α proteins of the present invention, preferably in the form of a sterile aqueous solution, is done peripherally, i.e., not intracranially, in a variety of waysincluding, but not limited to, orally, subcutaneously, intravenously, intranasally, transdermally, intraperitoneally, intramuscularly, intrapulmonary, vaginally, rectally, or intraocularly. In some instances, for example, in the treatment of wounds, inflammation, etc., the variant TNF-α protein may be directly applied as a solution, salve, cream or spray. The TNF-α molecules of the present may also be delivered by bacterial or fungal expression into the human system (e.g., WO 04046346 A2, hereby incorporated by reference).

Subcutaneous

Subcutaneous administration may be preferable in some circumstances because the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate. A TNF-α variant of the present invention may be more amenable to subcutaneous administration due to, for example, increased potency, improved serum half-life, or enhanced solubility.

Intravenous

As is known in the art, protein therapeutics are often delivered by IV infusion or bolus. The TNF-α variants of the present invention may also be delivered using such methods. For example, administration may be by intravenous infusion with 0.9% sodium chloride as an infusion vehicle.

Inhaled

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. TNF-α variants of the present invention may be more amenable to intrapulmonary delivery. TNF-α variants of the present invention may also be more amenable to intrapulmonary administration due to, for example, improved solubility or altered isoelectric point.

Oral Delivery

Furthermore, TNF-α variants of the present invention may be more amenable to oral delivery due to, for example, improved stability at gastric pH and increased resistance to proteolysis.

Transdermal

Transdermal patches may have the added advantage of providing controlled delivery of the DN-TNF-protein to the body. Dissolving or dispersing DN-TNF-protein in the proper medium can make such dosage forms. Absorption enhancers can also be used to increase the flux of DN-TNF-protein across the skin. Either providing a rate controlling membrane or dispersing DN-TNF-protein in a polymer matrix or gel can control the rate of such flux.

Intraocular

Ophthalmic formulations, eye ointments, powders, solutions and the like, are also contemplated as being within the scope of this invention.

In a preferred embodiment, variant TNF-α proteins are administered as therapeutic agents, and can be formulated as outlined above. Similarly, variant TNF-α genes (including both the full-length sequence, partial sequences, or regulatory sequences of the variant TNF-α coding regions) may be administered in gene therapy applications, as is known in the art. These variant TNF-α genes can include antisense applications, either as gene therapy (i.e. for incorporation into the genome) or as antisense compositions, as will be appreciated by those in the art.

In a preferred embodiment, the nucleic acid encoding the variant TNF-α proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. U.S.A. 83:4143-4146 (1986), incorporated entirely by reference). The oligonucleotides can be modified to enhance their uptake, e.g. by substituting their negatively charged phosphodiester groups by uncharged groups.

Dosage

Dosage may be determined depending on the disorder treated and mechanism of delivery. Typically, an effective amount of the compositions of the present invention, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 2000 mg per kilogram body weight per day. An exemplary treatment regime entails administration once every day or once a week or once a month. A DN-TNF protein may be administered on multiple occasions. Intervals between single dosages can be daily, weekly, monthly or yearly. Alternatively, A DN-TNF protein may be administered as a sustained release formulation, in which case less frequent administration is required. Dosage and frequency vary depending on the half-life of the agent in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity. Suitably, an effective amount (e.g., dose) of a DN-TNF protein described herein will provide therapeutic benefit without causing substantial toxicity to the subject. Toxicity of the agent described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in human. The dosage of the agent described herein lies suitably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: The Pharmacological Basis of Therapeutics, Ch. 1 (1975).

EXAMPLES

Example 1

Transmembrane Tumor Necrosis Factor is Neuroprotective

Animals -Mice containing a conditional IκB kinase β (IKKβ) allele in which exon 3 of the Ikbkb gene, encoding the IKKβ activation loop, is flanked by loxP sites (IKKβF/F) have previously been described (Park et. al. Science 2002; 297:2048-51; Li et al J Immunol 2003; 170:4630-7). Mice with a selective deletion of IKKβ in CNS neurons (nIKKβKO) were generated by crossing IKKβF/F mice with mice that express a neuronal calmodulin-kinase IIa promoter-driven Cre recombinase (CamkIICre; Minichiello et al. Neuron 1999; 24:401-24).

Experimental autoimmune encephalomyelitis induction and evaluation-EAE in female C57BL/6, IKKβF/F and nIKKβKO mice was induced by subcutaneous tail base injection of 30 μg of the 35-33 peptide sequence of rat myelin oligodendrocyte glycoprotein (MOG35-55) dissolved in 100 μl saline emulsified in an equal volume of complete Freund's adjuvant supplemented with 400 μg of H37Ra *Mycobacterium tuberculosis* (Difco). Mice also received an intraperitoneal injection of 200 ng of pertussis toxin (Sigma-Aldrich) on Days 0 and 2 post-immunization. Groups of mice were treated with twice weekly subcutaneous injections of XPro1595 (10 mg/kg; Xencor; Steed et al. Science 2003; 301:1895-8), etanercept (10 mg/kg; Amgen; Murray and Dahl, Ann Pharmacother 1997; 31:1335-8) or saline vehicle in either prophylactic (starting on the day of immunization) or therapeutic (starting at the onset of clinical signs) protocols. Mice were assessed daily for clinical signs of disease according to the following scale: 0, normal; 1, limp tail; 2, hind limb weakness; 3, hind limb paralysis; 4, forelimb weakness; and 5, moribund or dead (0.5 gradations represent intermediate scores). Moribund animals were sacrificed and given a clinical score of 5 for the remaining days of the experiment. Mice were allowed access to food and water ad libitum throughout the experiment.

Histopathological analysis—Mice were transcardially perfused with ice-cold 4% paraformaldehyde in phosphate-buffered saline under deep anaesthesia. CNS tissues were processed according to methods known in the art.

Biomarker analysis—Mouse brain, spinal cord and serum from representative mice were dissected and frozen in liquid nitrogen. Tissue homogenates and serum were analysed by multi-analyte profiling technology (Rules Based Medicine). Tissues were assayed using the RodentMAP® v. 2.0 multiplex immunoassays. Bead-based immunoassays were developed and optimized at Rules Based Medicine and read out on a Luminex 200 system (Luminex). The panel contained 59 biomarkers, including key cytokines, chemokines and proteases. Markers not shown for spinal cord versus brain and serum could not be assayed in spinal cord due to limited material.

T cell priming and proliferation assays—T cells were primed in vivo by subcutaneous immunization of C57BL/6 mice with 30 μg of MOG35-55 peptide dissolved in 100 μl saline and emulsified in an equal volume of complete Freund's adjuvant (Sigma-Aldrich) supplemented with 400 μg H37Ra *M. tuberculosis* (Difco). Draining lymph nodes and spleens were removed 10 days later. Isolated mononuclear cells were stimulated in triplicate at 4×106 cells/ml in round-bottom, 96-well plates (Costar) for 72 h in RPMI 1640 (Biochrom) containing 10% heat-inactivated foetal calf serum, 50 μM 2-mercaptoethanol and increasing concentrations of MOG35-55. Cells were pulsed with 0.5 μCi [3H]thymidine (Amersham Radiochemicals)/5×105 cells for the last 16 h of culture, and [3H]thymidine incorporation was measured by liquid scintillation counting (Wallac). Results are expressed as a stimulation index to MOG35-55 peptide (ratio between radioactivity counts of cells cultured in the presence of peptide and cells cultured with medium alone).

Extraction and characterization of central nervous system-infiltrating cells-Splenocytes and spinal cord-infiltrating mononuclear cells were isolated from mice at the peak of EAE and Day 35 post-immunization. Spinal cord mononuclear cells were isolated by Percoll gradient centrifugation as is known in the art. For detection of cell surface markers, cells were washed and fixed in 2% paraformaldehyde solution in phosphate-buffered saline for 15 min at room temperature and stained with fluorochrome-labelled antibodies (anti-NK1.1, clone PK136; anti-CD11b/Mac1, clone M1/70; BD Biosciences). For detection of the CD4 surface marker and intracellular cytokines by fluorescence-activated cell sorting analysis, after isolation, cells were restimulated with 10 ng/ml phorbol 12-myristate 13-acetate and 1 μg/ml ionomycin in the presence of 5 μg/ml brefeldin A (Sigma-Aldrich) for 3 h before fixation, as above. Cells were permeabilized with 0.5% w/v saponin and stained with fluorochrome-labelled antibodies (anti-CD4, clone L3T4; anti-IFN-γ, clone XMG1.2; anti-IL-17, clone TC11-18H10; BD Biosciences). Data acquisition and analysis were done with a FACSCalibur cytometer and CellQuest software (BD Biosciences).

Neuron/astrocyte cultures and experimental treatments—Astrocyte cultures were prepared from post-natal Days 1-3 cortical tissues of C57BL/6 mice by mild mechanical trituration. Cells were grown on poly-D-lysine (0.1 mg/ml) and laminin (20 μg/ml)-coated 24-well plates in medium containing Dulbecco's Modified Eagle Medium containing 4.5 g/L glucose and supplemented with 10% foetal calf serum, 10% horse serum, 2 mM Glutamax, 1 mM sodium pyruvate, 100 μM non-essential amino acids, 50 U/ml penicillin and 50 μg/ml streptomycin. A confluent layer of astrocytes was used as a feeder layer for primary cortical neurons. Cortical neurons were prepared from embryonic Day 15 mice as previously described (Nicole et al. J Neurosci 2001; 21:3024-33), plated on the astrocyte feeder layer, and used for experiments starting on neuronal Days 7 and 8 in vitro. Glucose deprivation was performed as previously described (Taoufik et al. J Neurosci 2007; 27:6633-46). Human recombinant TNF (R&D; 50 ng/ml), which selectively signals through murine TNF receptor I and is sufficient to activate murine astrocytes, was added to co-cultures 24 h prior to the onset of and during glucose deprivation. XPro 1595 (Xencor; 200 ng/ml; Steed et al., 2003) or etanercept (Amgen; 100 ng/ml; Murray and Dahl, 1997) was added to the co-cultures 4 h after the onset of glucose deprivation. BMS 345 541 (Merck; 25 μM) was added to the co-cultures 2 h before glucose deprivation. Mixed cultures were stained with 0.4% trypan blue dye solution (Sigma) and cells were considered viable if they excluded the dye. Cells with neuron morphology were counted in 10 different fields per well, in at least three separate cultures per condition, by phase contrast microscopy (×40 objective).

RNA isolation and semi-quantitative reverse transcription-polymerase chain reaction—Total RNA was extracted with TRIzol® (Invitrogen) according to the manufacturer's instructions. For semi-quantitative reverse transcription-polymerase chain reaction (RT-PCR), DNase-treated (Promega) RNA was reverse transcribed with M-MLV Reverse Transcriptase (Promega) and random hexamers (Roche). Primers were used for the detection of FLICE-inhibitory protein (FLIP) (forward: 5'-GAA GAG TGT CTT GAT GAA GA-3' (SEQ ID NO:4) and reverse: 5'-GAA AAG CTG GAT ATG ATA GC-3' (SEQ ID NO:5)), vascular endothelial growth factor (forward: 5'-GCG GGC TGC CTC GCA GTC-3' (SEQ ID NO:6) and reverse: 5'-TCA CCG CCT TGG CTT GTC AC-3' (SEQ ID NO:7)) and colony stimulating factor-1 receptor (forward: 5'-GAC CTG CTC CAC TTC TCC AG-3' (SEQ ID NO:8) and reverse: 5'-GGG TTC AGA CCA AGC GAG AAG-3' (SEQ ID NO:9)). Mouse β-actin was amplified as a loading control. Densitometric analysis was performed using Image Quant 5.2 (Molecular Dynamics Storm Scanner 600) and relative band intensities were determined.

Western blot analysis—Total protein extracts from spinal cords of selected mice were prepared as previously described (Taoufik et al., 2007). Thirty micrograms of total protein extracts were resolved on NuPAGE Novex Bis-Tris Gels (Invitrogen) and transferred onto nitrocellulose membranes (Schleicher and Schuell). Blots were probed with antibodies against the non-phosphorylated form of neurofilament-H (SMI-32) (1:400, Covance), glial fibrillary acidic protein (1:1500, Chemicon), myelin basic protein (1:200, Chemicon), phospho-IκBα (1:500, Cell Signalling), phospho-p65 (1:250, Cell Signalling) and caspase 3 (1:2000, Santa Cruz). The secondary antibodies used were horseradish peroxidase-conjugated anti-mouse and anti-rabbit IgG (1:2000 up to 1:5000, Jackson Immunoresearch Laboratories). Antibody binding was detected using the ECL Plus detection system (Amersham Pharmacia). To normalize for protein content, membranes were stripped and reprobed with anti-β-tubulin antibody (1:1000, Pharmingen).

Statistical analysis—Statistical analyses were performed with Sigma Stat 2.0 for Windows. All data are given as mean±SEM. To compare clinical scores among treated groups of mice at each time point and neuropathological changes (inflammation, demyelination, axon dystrophy and axon loss), the Mann-Whitney rank sum test was performed. For biomarker analysis, Student's t-test was performed. For semi-quantitative protein and RT-PCR analyses, a measurement of the band intensity was performed with ImageQuant 5.2 (Molecular Dynamics Storm Scanner 600) and expressed as pixel intensity per unit area. Values were normalized using the β-actin or β-tubulin values, respectively, and were compared using one-way ANOVA followed by Bonferroni t-test for pair-wise comparisons. For cell viability, ANOVA on Ranks followed by Bonferroni t-test for pair-wise comparisons was used. Fluorescence-activated cell sorting analysis and proliferative responses of splenocytes and lymph node cells were analysed by Mann-Whitney rank sum test. P<0.05 were considered statistically significant.

Results—Inhibition of soluble tumour necrosis factor, but not soluble and transmembrane tumour necrosis factor, protects mice against experimental autoimmune encephalomyelitis EAE was induced in female C57BL/6 mice by immunization with MOG35-55 peptide and the effects of twice weekly subcutaneous injection of XPro1595 (10 mg/kg), or etanercept (10 mg/kg) or of saline vehicle were tested in both prophylactic (starting on the day of immunization) and therapeutic (starting at the onset of clinical signs) protocols. Both inhibitors have been characterized previously to show equivalent potency and effectiveness in a murine model of rheumatoid arthritis *Listeria monocytogenes* infection (Zalevsky et al. J Immunol 2007; 179:1872-83). XPro1595 provided significant clinical benefits compared with control in both therapeutic (FIG. 3A and Table 1) and prophylactic (FIG. 3B and Table 1) protocols, demonstrating disease-promoting effects of soluble TNF. In contrast, inhibition of both soluble TNF and transmembrane TNF with etanercept did not provide benefit when compared with controls in either treatment protocols and even exacerbated disease. Comparison between the two treatment groups showed that etanercept-treated mice displayed significantly increased clinical defects compared with XPro1595-treated mice (FIGS. 3A and B; Table 1), indicating that transmembrane TNF exerts significant beneficial effects in EAE. Mice-treated prophylactically with either XPro1595 or etanercept showed a significant delay in disease onset (FIG. 3B and Table 1) confirming a disease-advancing role for soluble TNF.

TABLE 1

Incidence, clinical severity and mortality rate of $MOG_{35-55}$ induced EAE in vehicle-, XPro1595- and etanercept-treated mice

| Mice | Incidence (%) | Day of onset, mean ± SEM | Maximal score, mean ± SEM | Clinical score at first peak, mean ± SEM | Cumulative score (up to day post-immunization) | Mortality rate (%) |
|---|---|---|---|---|---|---|
| Therapeutic Experiment 1 | | | | | | |
| Vehicle | 8/8 (100) | 14.75 ± 0.79 | 4 ± 0.33[a] | 2.57 ± 0.39 | 614 (53) | 3/8 (38) |
| XPro1595 | 6/9 (67) | 15.8 ± 1.07 | 2.14 ± 0.95[b] | 1.31 ± 0.51[b] | 343 (53) | 2/6 (33.3) |
| Etanercept | 8/8 (100) | 15.63 ± 0.99 | 4.57 ± 0.28 | 2.93 ± 0.41 | 836 (53) | 5/8 (62.5) |
| Experiment 2 | | | | | | |
| Vehicle | 10/10 (100) | 10.4 ± 0.73 | 4 ± 0.4 | 3.1 ± 0.38 | 832 (39) | 3/10 (30) |
| XPro1595 | 10/10 (100) | 11.2 ± 0.51 | 2.75 ± 0.16 | 2.25 ± 0.13[b] | 565 (39) | 0/10 (0) |
| Etanercept | 10/10 (100) | 10.7 ± 0.21 | 4 ± 0.32 | 3.1 ± 0.27 | 737 (39) | 3/10 (30) |
| Prophylactic | | | | | | |
| Vehicle | 10/10 (100%) | 11.3 ± 0.49[c] | 3.4 ± 0.38 | 2.85 ± 0.38 | 754 (41) | 1/10 (10) |
| XPro1595 | 10/10 (100%) | 17.2 ± 1.21 | 4 ± 0.47 | 2.7 ± 0.33 | 671 (41) | 3/10 (30) |
| Etanercept | 10/10 (100%) | 15.33 ± 0.44 | 4.25 ± 0.15 | 3.56 ± 0.15 | 698 (41) | 2/10 (20) |

[a]P < 0.05 for comparison between mice treated with vehicle or XPro1595.
[b]P < 0.05 for comparison between mice treated with XPro1595 or etanercept.
[c]P < 0.05 for comparison between mice treated with vehicle or XPro1595 and vehicle or etanercept.

Figure 4:
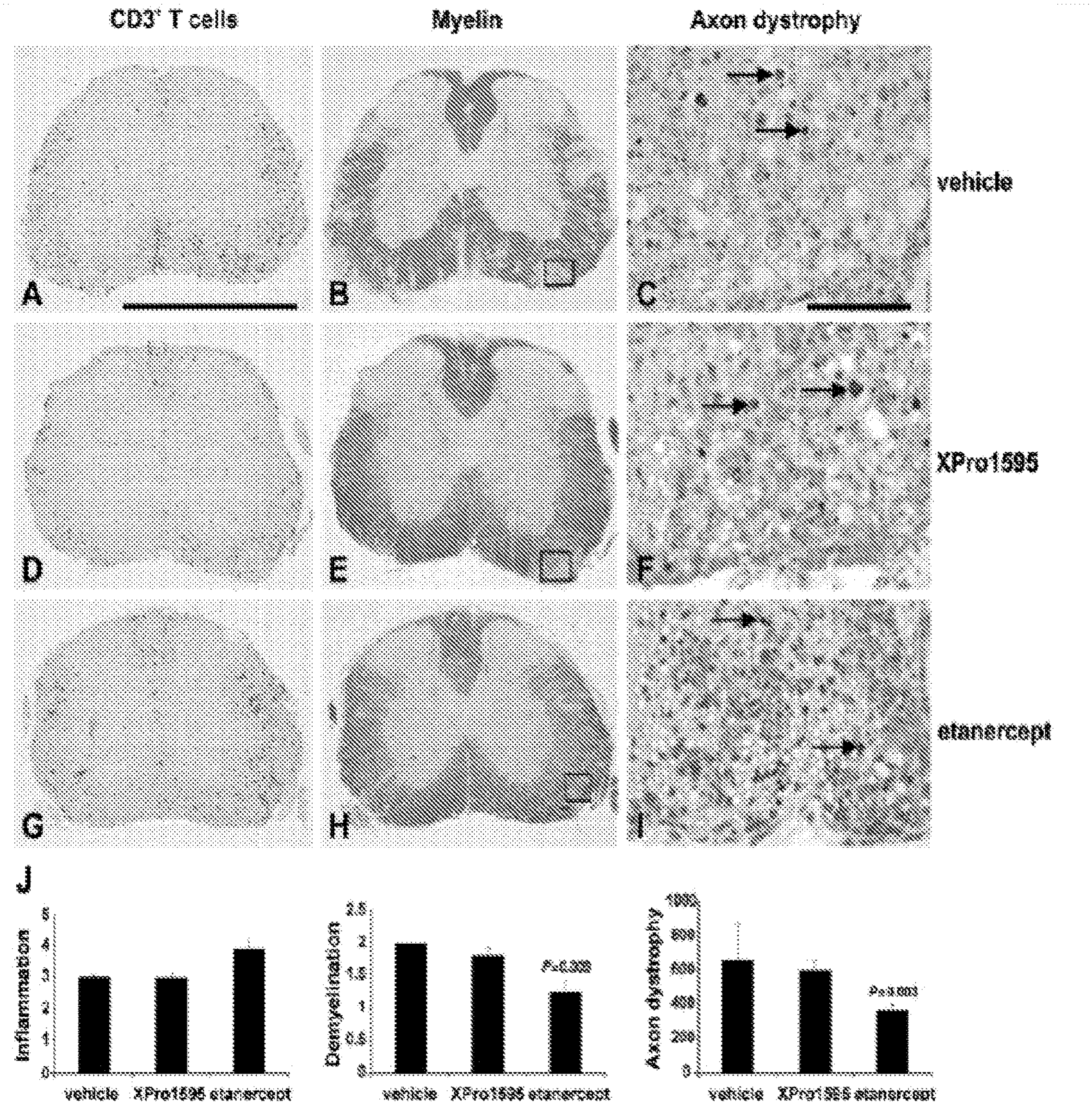
FIG. 4—TNF inhibitors do not alter the extent of inflammatory cell infiltration in the spinal cord at EAE peak.

Spinal cord sections taken at disease peak in the vehicle group (FIG. 4) and Day 35 post-immunization with MOG peptide, when block of soluble TNF with XPro1595 gave maximal protection, showed equivalent levels of inflammatory cell infiltration and similar lesion size in the different treatment groups at both time points, as measured at peak by immunostaining for CD3 (FIGS. 4A, D and G) and Day 35 post-immunization by haematoxylin and eosin staining. The area of local structural damage in lesions, as measured by Luxol fast blue staining for demyelination (FIGS. 4B, E and H) and the number of amyloid precursor protein-immunostained dystrophic axons in the anterior column (FIGS. 4C, F and I), was also similar in XPro1595-treated compared with vehicle-treated samples at both time points. Surprisingly, myelin and axon damage were reduced in etanercept-treated compared with vehicle-treated samples at peak (FIGS. 4B, C, H and I), but not Day 35 post-immunization, even though these mice presented the most severe clinical scores. These results revealed a dissociation between the effects of TNF inhibitors on clinical disease and on early inflammatory spinal cord lesions, and indicate that the therapeutic benefit of soluble TNF inhibition is at least partly independent of levels of initial CNS infiltration by inflammatory cells.

Tumour necrosis factor blockade does not compromise MOG35-55-specific effector T cell responses Next examined was whether TNF blockade affected immune responses by analysing primary T cell responses to MOG35-55 in mice that had soluble TNF, or soluble TNF and transmembrane TNF, blocked. No significant differences in the recall proliferation responses of splenocytes or of draining lymph node cells to MOG35-55 or maturation of CD4+ IFN-γ+ and CD4+IL-17+ effector T cells in spleen-were detected among the different treatment groups. Also compared was secondary T cell responses to MOG35-55 in splenocytes and spinal cord-infiltrating mononuclear cells isolated from mice at peak and chronic phases of EAE. Again, no differences in splenocyte or CNS-infiltrating CD4+ IFN-γ+ T cells, CD11b+ cells or NK1.1+ were detected among the treatment groups, except for an increase in CD4+IFN-γ+ splenocytes in XPro1595-treated versus vehicle-treated mice at peak. Thus, overall immune responses are not affected by either of the TNF inhibitors.

Figure 5:
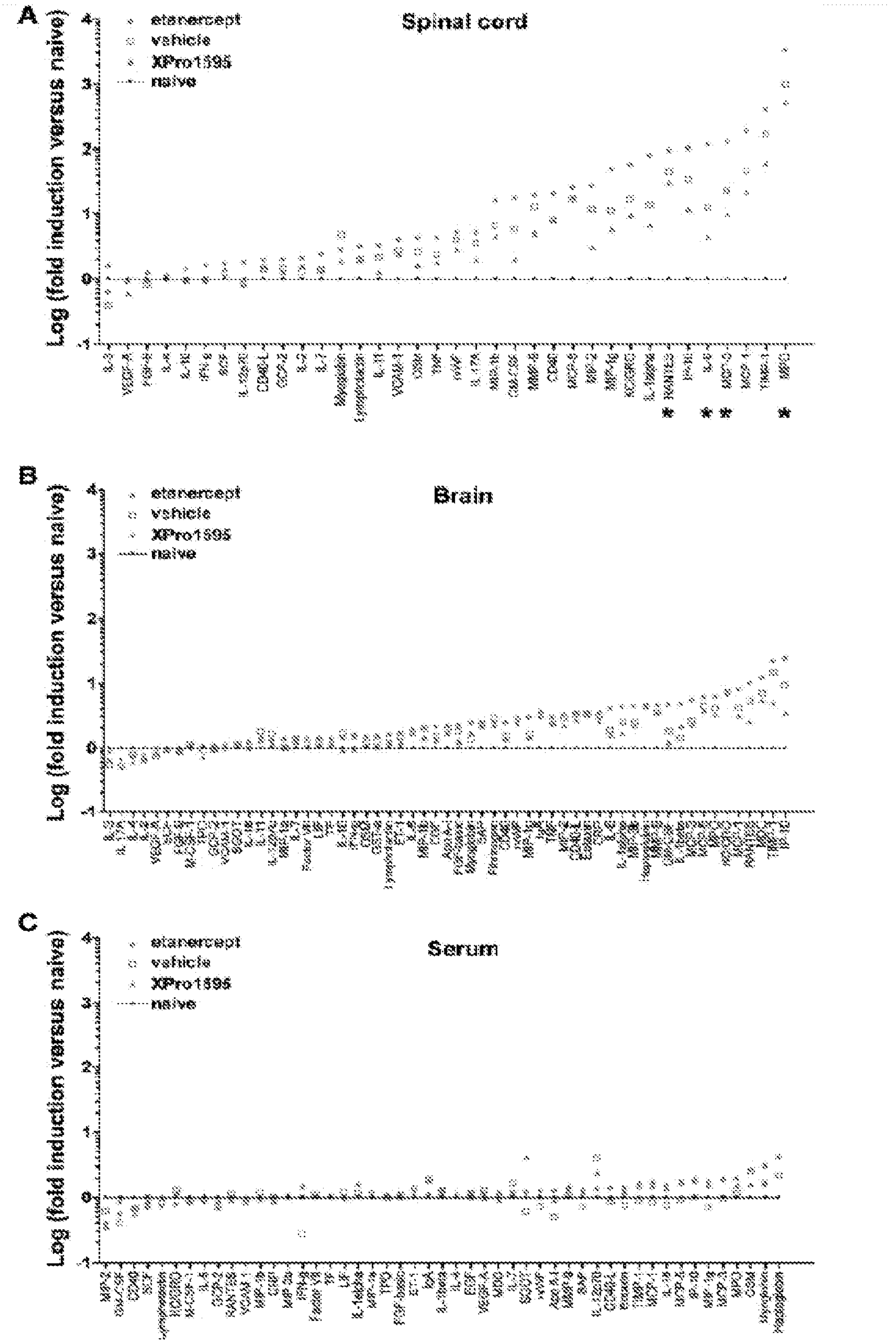
FIG. 5—Non-selective TNF inhibition exacerbates, and soluble TNF-selective inhibition suppresses, inflammation markers in the CNS at EAE peak. Multiplex immunoassay analysis of 59 key protein markers was done on spinal cord (A), brain (B) and serum (C) of naive and three treatment groups of EAE mice at peak of disease. Mean is shown for XPro1595 (green triangle) and etanercept (red circle) (n=3 mice per group); for naïve (dotted line) and vehicle (open square) (n=2 mice per group).

Inhibition of soluble tumour necrosis factor, not soluble and transmembrane tumour necrosis factor, reduces the production of pro-inflammatory mediators and chemokines in the central nervous system To explore mechanisms that might mediate the differences in clinical score between treatment groups, we performed a broad biomarker analysis on naïve mice and EAE mice treated with vehicle or TNF blockers, at the time of disease peak in the vehicle group. A standard biomarker panel from Rules Based Medicine was used to quantitatively assess expression of 59 key protein markers in whole brain and spinal cord extracts and serum. Many pro-inflammatory and chemotactic molecules showed upregulation in the spinal cord (FIG. 5A) and brain (FIG. 5B) but not serum (FIG. 5C) of vehicle-treated EAE compared with naïve mice with similar expression patterns, although the amplitude of effects was greater in the spinal cord. Notably, a large number of these molecules are products of activated macrophages/microglia (MPO, MCP-1/CCL2, RANTES, IL-1, KC/GRO/CXCL1; Muhagishi et al. J Neuroimmunol 1997; 77:17-26; Filipovic et al. Dev Neurosci 2003; 25:279-90; Simi et al. Biochem Soc Trans 2007; 35:1122-6; Gray et al. Brain Pathol 2008; 18:86-95) and astrocytes (MCP-1, MCP-3/CCL7, IP-10, RANTES, KC/GRO; Ransohoff et al. FASEB J 1993; 7:592-600; Mihagishi et al. J Neuroimmunol 1997; 77:17-26; Omani et al. Glia 2006; 53:24-31; Thompson and Van Eldik Brain Res 2009; 1287:47-57) under conditions of inflammation; several are key mediators of EAE (MPO, MCP-1, IL-6; Eugster et al. Eur J Immunol 1999; 29:626-32; Mahad and Ransohoff Semin Immunol 2003; 15:23-32; Chen et al., Brain 2008; 131:1123-33) and are upregulated in multiple sclerosis tissues (MPO, MCP-1, KC/GRO; Filipovic et al.; Mahad and Ransohoff; Omari et al.; Gray et al.). Interestingly, inhibition of soluble TNF and transmembrane TNF by etanercept further enhanced expression of several of these mediators in the spinal cord (FIG. 5A) and brain (FIG. 5B) compared with vehicle-treated EAE mice. In contrast, selective soluble TNF inhibition by XPro1595 generally reduced expression relative to vehicle-treated mice in both spinal cord (FIG. 5A) and brain (FIG. 5B). These results show that transmembrane TNF acts to downregulate the production of pro-inflammatory mediators within CNS tissues during EAE, while soluble TNF increases their expression.

Figure 6:
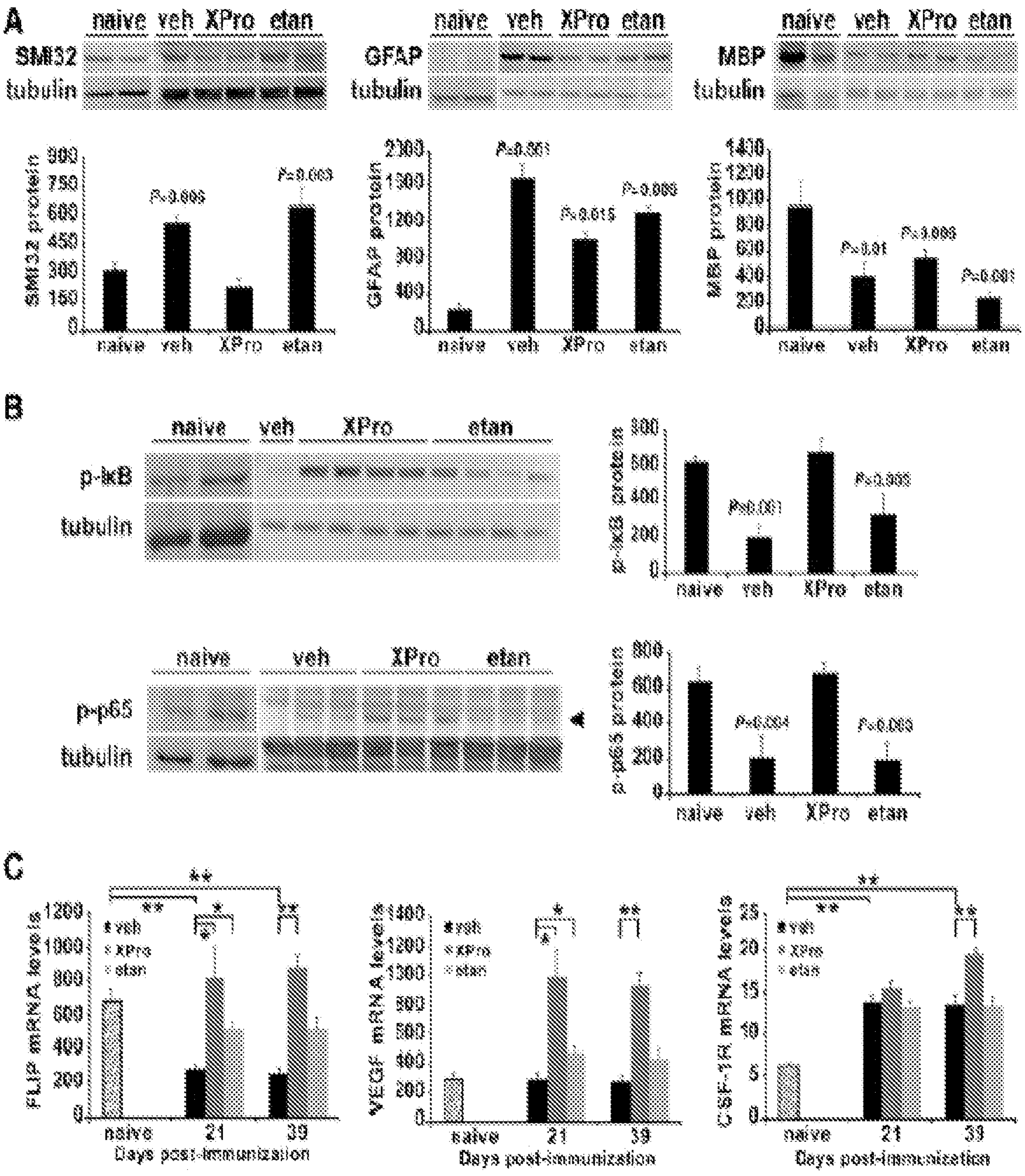
FIG. 6—Blockade of soluble TNF, but not soluble TNF and transmembrane TNF, is sufficient to maintain NF-κB activity and expression of other neuroprotective mediators in the spinal cord during EAE. (A) Immunoblot analysis of SMI-32, glial fibrillary acidic protein (GFAP) and myelin basic protein (MBP) expression in extracts of spinal cord from naïve and treated EAE mice at disease peak. (B)

Inhibition of soluble tumour necrosis factor, not soluble and transmembrane tumour necrosis factor, maintains the expression of neuroprotective proteins in the spinal cord Immunoblot and densitometry analysis of total spinal cord lysates from naïve and treated EAE mice at disease peak for CNS cell marker proteins showed that levels of the non-phosphorylated form of neurofilament-H (SMI-32), a marker of neurodegeneration, and glial fibrillary acidic protein, a marker of astrocytosis, were significantly upregulated in both vehicle-treated and soluble TNF plus transmembrane TNF blocker (etanercept)-treated compared with naïve tissue (FIG. 6A). In contrast, soluble TNF blocker (XPro1595)-treated tissues showed no changes in SMI-32 levels compared with naïve tissue and a smaller upregulation of glial fibrillary acidic protein compared with vehicle- and etanercept-treated tissue (FIG. 6A). Levels of myelin basic protein were markedly reduced in tissues from all treatment groups compared with naïve, although this change was again less severe in XPro1595-treated compared with vehicle- and etanercept-treated tissues (FIG. 6A).

Next analyzed were the phosphorylated forms of the inhibitor of NF-κB, which becomes degraded thereby releasing active NF-κB, and of the p65 subunit of NF-κB, which is specifically induced by TNF and associated with TNF-mediated neuroprotection. The levels of both phosphorylated inhibitor of NF-κB and phosphorylated p65 NF-κB subunit were significantly reduced in vehicle- and etanercept treated compared with naïve spinal cord, implying lower levels of NF-κB activity. However, blocking the activity of soluble TNF with XPro1595 treatment maintained the phosphorylation levels of these proteins close to those in naïve tissue (FIG. 6B). This shows that soluble TNF contributes to the loss of spinal cord NF-κB activity and that transmembrane TNF has an opposing effect during EAE.N Next compared was expression of the NF-κB-induced neuroprotective proteins FLIP and vascular endothelial growth factor, and of the receptor for colony stimulating factor-1, CSF-1R, by semi-quantitative RT-PCR of total RNA isolated at peak and Day 39 post-immunization (FIG. 6C). FLIP expression was significantly reduced in vehicle-treated spinal cord at both EAE time points compared with naïve tissue (FIG. 6C). In contrast, its expression was preserved in XPro 1595- and etanercept-treated cord, showing that soluble TNF contributes to EAE-induced loss of FLIP expression. Pair-wise analysis between treatment groups at each time point showed that the soluble TNF blocker XPro1595 was more effective than etanercept at maintaining FLIP levels in the spinal cord during EAE, indicating that transmembrane TNF is sufficient for this. Vascular endothelial growth factor expression was not altered in vehicle-treated spinal cord during EAE compared with naïve tissue (FIG. 6C). However, pair-wise analysis between groups at each time point showed marked upregulation of expression in XPro1595-treated tissues at both time points, and in etanercept-treated tissues at peak, showing that soluble TNF inhibits vascular endothelial growth factor induction during EAE and that XPro1595 most effectively blocks this inhibition (FIG. 6C). Colony stimulating factor-1 receptor expression was induced in the spinal cord during EAE independently of treatment, although XPro1595 further enhanced its expression at Day 39 post-immunization (FIG. 6C). These results show that inhibition of soluble TNF and maintenance of transmembrane TNF with XPro1595 supports the expression of neuroprotective molecules in the spinal cord during EAE.

Transmembrane tumor necrosis factor mediates neuroprotection against glucose deprivation in astrocyte-neuron co-cultures To examine whether the protective effects of transmembrane TNF in EAE include the enhanced survival of neurons, we studied the effects of TNF blockade in astrocyte-neuron co-cultures subjected to glucose deprivation-induced death, a model for ischaemic neuronal damage that has relevance to multiple sclerosis (Lassmann J Neurol Sci 2003; 206:187-91). Astrocytes were included as a source of murine transmembrane TNF and soluble TNF. As previously shown in nearly pure cortical neuron cultures (<5% astrocytes; Taoufik et al., 2007), glucose deprivation induced the death of neurons that were cultured in direct contact with astrocytes, and this was inhibited by soluble TNF blockade (XPro1595), but not soluble TNF plus transmembrane TNF blockade (etanercept) starting 4 h after the onset of glucose deprivation (FIGS. 7A and B). Astrocyte viability was not affected by glucose deprivation. To activate astrocytes and to induce the production of transmembrane TNF, astrocyte-neuron co-cultures were pretreated with human TNF for 24 h prior to glucose deprivation, conditions that induce strong neuroprotection in nearly pure neuronal cultures (Taoufik et al., 2007). These conditions significantly reduced glucose deprivation-induced neuronal death, and this protection was inhibited by etanercept but not XPro1595, indicating that it is mediated by transmembrane TNF. A neuroprotective role for induced transmembrane TNF was further confirmed by the finding that XPro1595-treated cultures showed less neuronal death after human TNF pretreatment (FIG. 7B). When neurons were cultured with astrocytes separated from them by Transwells, however, soluble TNF blockade (XPro1595) starting 4 h after the onset of glucose deprivation was ineffective in protecting neurons against glucose deprivation-induced death (FIG. 7C). This shows that transmembrane TNF neuroprotection is dependent upon astrocyte-neuron contact and that astrocytes are the source of neuroprotective transmembrane TNF under these conditions Immunoblot and densitometry analysis for phosphorylated inhibitor of NF-κB and the phosphorylated p65 NF-κB subunit of NF-κB showed that, as in EAE spinal cord, their levels were maintained in XPro1595-treated, but not etanercept-treated, glucose deprivation-challenged astrocyte-neuron cultures when measured 24 h after glucose deprivation. Levels of active caspase 3 (p20 subunit) were also significantly reduced in XPro1595-compared with etanercept-treated cells at 12 h after glucose deprivation.

Transmembrane tumor necrosis factor-mediated protection in experimental autoimmune encephalomyelitis is dependent upon neuronal NF-κB activity Next tested was whether transmembrane TNF-mediated neuroprotection through NF-κB signalling in neurons may be one mechanism of XPro1595's clinical efficacy in vivo in the EAE model. In a previous study, we showed that neuronal IKKβ, which phosphorylates and mediates the degradation of IκB, thereby activating NF-κB (Ghosh and Karin 2002), is sufficient to mediate neuroprotection and suppression of CNS inflammation in EAE. Here, we tested whether XPro 1595 was capable of exerting its therapeutic effects in conditional IKKβ mice that selectively lack IKKβ in CamkII-expressing neurons in the brain and spinal cord (nIKKβKO). Similar to results in wild-type C57BL/6 mice, control IKKβF/F mice, in which exon 3 of the Ikbkb gene is flanked by loxP sites but not deleted by Cre recombinase, were protected from the clinical symptoms of EAE during the chronic phase by XPro1595 administration (FIG. 8A). In contrast, XPro1595 administration provided no protection in nIKKβKO mice, and disease followed a severe non-remitting course in both vehicle- and XPro1595-treated groups until the last time point studied (FIG. 8A). Beneficial effects of XPro1595 in IKKβF/F, but not nIKKβKO, mice were also seen on animal survival (FIG. 8B). Consistent with these results, a selective IKKβ inhibitor, BMS 345 541, abolished the neuroprotective effects of XPro1595 against glucose deprivation in neuron-astrocyte co-cultures (FIG. 8C), possibly through combined inhibition of astrocyte activation (and therefore beneficial transmembrane TNF production) and neuroprotection. Overall, these results show that the therapeutic effects of the soluble TNF blocker XPro1595 in EAE are directly dependent upon neuronal NF-βB activity, and suggest that transmembrane TNF is a neuroprotective mediator that signals via neuronal NF-κB to induce CNS tolerance and possibly also repair during the chronic phase of EAE.

Example 2

Peripheral Administration of XPro1595 DN-TNF in AAV-Asyn Rat Model of Parkinson's Disease Intranigral injections of rAAV will be used to overexpress human A-syn in DA neurons to achieve pathological mishandling of A-syn that results in significant DA cell death in SN. A second group of animals will receive rAAV-GFP as a negative control. Three days after AAV injections, these two groups will be further divided to receive peripheral administration of DN-TNF XPro 1595 or formulation buffer. To evaluate the extent to which neutralization of solTNF in the periphery attenuates central neuroinflammation and degeneration of nigral DA neurons, rats will be assessed for motor performance weekly for 4 weeks after which brains will be harvested for immunohistological analyses for stereological estimates of nigral DA neuron number, microglia and TNF pathway activation, and T cell infiltration. Cytokines and chemokines expression profiles will also be analyzed at an intermediate timepoint.

Surgery: Two groups of rats (n=40×2) will receive unilateral 2 μl injections under stereotaxic guidance of high titer rAAV encoding for either rAAV-GFP or rAAV-wt-a-syn into the right SN (AP: −5.3 mm, ML: −2.1 mm relative to bregma, DV: −7.2 mm ventral relative to dura). Three days post-surgery half of the animals will begin receiving twice weekly subcutaneous injections of XPro1595 (10 mg/kg) and the other half with formulation buffer as control. Dosing is based on Tmax (serum) for s.c. dose of ~18 hr in rats.

Animal sacrifice and tissue processing: 6 animals from each group will be sacrificed at 4 weeks and 8 per group at 9-10 weeks post-rAAV injection. Animals will be deeply anesthetized and perfused with 4% paraformaldehyde. Brains will be harvested and cryosectioned on a freezing microtome for immunohistochemical analysis. For cytokine analyses at 4 weeks, 6 rats per group will be sacrificed and SN and striata rapidly microdissected and kept at −80C until analyses.

Behavior Testing. Animals will be test for motor performance at 4 and 8 weeks using the cylinder and stepping test; rAAV-Asyn injected rats have been shown to display motor deficits in both tasks (Romero-Ramos, unpublished).

Microglia and TNF Pathway Activation. Immunohistochemistry for microglial markers (Iba1, CD68 and MHCII) and TNF pathway activation (phospho-FADD, phospho-TRADD) will be performed at the level of striatum and SN and analyzed by immunofluorescence microscopy by an investigator blinded to treatment history. Assessment of the cell number will be done by unbiased stereological quantification of Iba1+ cells in the AAV-Syn (or AAV-GFP) injected side and comparison with the uninjected contralateral site. In addition, T cell infiltration will be analyzed by immunostaining of CD8+ and CD4+ cells.

Nigral DA neuron number Immunohistochemistry for the dopaminergic marker (tyrosine hydroxylase) and pan-neuronal marker (NeuN) will be performed at the level of the SN. Assessment of the cell loss will be done by unbiased stereological quantification of the remaining DA neurons in the SN versus the uninjected site.

Inflammatory Factor Profile. The SN and striata dissected at 4 weeks will be isolated and mRNA obtained for real-time PCR analyses of cytokine/chemokine expression (Rat Inflammatory Cytokines & Receptors PCR Array, SABiosciences). Validation of dysregulated genes will be performed by real time PCR.

Example 3

Peripheral Administration of XPro1595 DN-TNF in 6-OHDA Rat Model of Parkinson's Disease Unilateral injections of 6-OHDA will be used to induce retrograde degeneration of nigral DA neurons in young adult rats. A second group of animals will receive a mock (saline) lesion as negative control. Three days after striatal injections, these two groups will be further divided to receive peripheral administration of DN-TNF XPro1595 or formulation buffer. To evaluate the extent to which neutralization of solTNF in the periphery attenuates central neuroinflammation and degeneration of nigral DA neurons, rats will be assessed for motor performance weekly for 4 weeks after which brains will be harvested for immunohistological analyses for stereological estimates of nigral DA neuron number, microglia and TNF pathway activation, and T cell infiltration. Cytokines and chemokines expression profiles will also be analyzed at an intermediate timepoint.

Surgery: Two groups of rats (n=40×2) will receive unilateral injections of 4 ul 6-OHDA (20 ug) under stereotaxic guidance using published protocols (Harms et al., 2011) at the rate of 0.5 μl/minute into the right striatum (AP: −1.0 mm, ML: −3.0 mm relative to bregma, DV: −4.5 mm ventral relative to dura). Three days post-surgery half of the animals in the 6-OHDA and mock-lesioned groups will begin receiving twice weekly subcutaneous injections of XPro1595 (10 mg/kg) and the other half will receive formulation buffer as negative control. Dosing is based on Tmax (serum) for s.c. dose of ~18 hr in rats.

Animal sacrifice and tissue processing: 6 animals from each group will be sacrificed at 2 weeks (end of acute phase of nigral cell death) and 8 per group at 5 weeks (end of the progressive phase of nigral cell death) post striatal 6-OHDA (or saline) injections. Animals will be deeply anesthetized and perfused with 4% paraformaldehyde. Brains will be harvested and cryosectioned on a freezing microtome for immunohistochemical analysis. For cytokine analyses at 5 weeks, 6 rats per group will be sacrificed and SN and striata rapidly microdissected and kept at −80 C until analyses.

Behavior Testing. Animals will be test for motor performance every other week for 5 weeks, using the cylinder and stepping test, both test have previously been shown by our lab to be affected in the 6-OHDA rat model (Harms et al., 2011).

Microglia Activation. Immunohistochemistry for microglial markers (Iba1, CD68 and MHCII) and TNF pathway activation (phospho-FADD, phospho-TRADD) will be performed at the level of striatum and SN and analyzed by immunofluorescence microscopy by an investigator blinded to treatment history. Assessment of the cell number will be done by unbiased stereological quantification of Iba1+ cells in the 6-OHDA (or saline) injected side and comparison with the uninjected contralateral site. In addition, T cell infiltration will be analyzed by immunostaining of CD8+ and CD4+ cells.

Nigral DA neuron number Immunohistochemistry for the dopaminergic marker (tyrosine hydroxylase) and pan-neuronal marker (NeuN) will be performed at the level of the SN. Assessment of the cell loss will be done by unbiased stereological quantification of the remaining DA neurons in the SN versus the uninjected site.

Inflammatory Factor Profile. The SN and striata dissected at 4 weeks will be isolated and mRNA obtained for real-time PCR analyses of cytokine/chemokine expression (Rat Inflammatory Cytokines & Receptors PCR Array, SABiosciences). Validation of dysregulated genes will be performed by real time PCR.

Example 4

Peripheral Administration of XPro1595 DN-TNF in the SOD1 Murine Model of ALS

Subjects. Animal models of inherited neurological diseases have significantly advanced our understanding of the molecular pathogenesis and hold great promise for developing potential therapeutic strategies for translation to patients. The development of transgenic mice expressing G93A human SOD1 as a mouse model for the human disease has been regarded as a major breakthrough for development of ALS therapeutics. G93A SOD1 transgenic mice develop progressive hind limb weakness, muscle wasting, and neuropathological sequelae similar to those observed in patients with both sporadic and familial ALS. The spinal cord of the G93A SOD1 mouse shows progressive reactive astrogliosis, marked neuronal atrophy, neuronal loss, and the presence of prominent ubiquinated inclusion bodies by 90 days of age. In addition, motor performance deteriorates as the disease progresses. The G93A SOD1 mouse model has played a prominent role in studying disease progression and especially for testing potential therapeutic agents, the latter in part because these animals have a shortened life span of approximately 126 days.

In the present study, G93A SOD1 mice and littermate controls are bred from existing colonies at the Bedford VA Medical Hospital. The male G93A SOD1 mice are mated with B6SJL females and the offspring are genotyped by PCR using tail DNA. The number of SOD1 transgenes are assessed by PCR to ensure that transgene copy number remains constant. Mice are housed in micro-isolator cages in complete barrier facilities, and all studies are performed in these facilities. A 12 hour light-dark cycle is maintained and animals are given free access to food and water. Control and transgenic mice of the same age (±2 days) and from the same 'f generation will be selected from multiple litters to form experimental cohorts (n=20 per group). Standardized criteria for age and parentage will be used for placing individual mice into experimental groups/cohorts. Wild type mice will be used for initial toxicity, tolerability, and pharmacokinetic studies and ALS mice will be used for one-month tolerability studies.

Tolerability, Dosing, and Pharmacokinetics. The tolerable dose range and LD50 for XPro1595 DN-TNF will be determined in wild type mice by increasing the dose b.i.d. one-fold each injection. The route of administration will be via i.p. administration. One goal is to select a range of doses for the efficacy study starting ten fold below the maximum tolerated dose. Initial pharmacokinetic (pK) studies will be conducted by giving animals a single dose, sacrificing them after 30 min, 1 h, 2 h, 4 h, 6 h, and 12 h, and dissecting brains and spinal cords and determining drug concentration in the target tissue. Drug steady-state level is determined in animals that had been dosed for 1 week prior to sacrifice. The range of dosing levels of 0.01, 0.1, and 1 mg/kg once a day will be administered throughout the lives of the G93A mice.

Behavioral pharmacology. Behavioral testing for the transgenic G93A SOD1 mice will be performed during the light phase of the diurnal cycle since these mice are sufficiently active during that time. Measurements will be taken for 30 minutes after 10 minutes of acclimation to the box (Opto-Varimex Unit, Columbus Instruments, Columbus, Ohio, USA). Counts of horizontal and vertical motion activity will be monitored and quantitative analysis of locomotor activity (resting and ambulatory times), will be assessed. The open field box will be cleaned before testing each mouse. Each 30 minutes of testing will be analyzed as three periods of 10 minute intervals to study the influence of novelty and measured behavior. Mice will be coded and investigators will be blinded to the genotype and analysis. Testing will be on week 4 and performed every other week until the mice could no longer participate.

Efficacy studies. Efficacy will be measured using endpoints that clearly indicate neuroprotective function. These include amelioration of degenerative changes in the spinal cord, improved motor function, and prolonged survival. Some mice cohorts will be sacrificed at a predetermined time point (120 days) for neuropathological examination, while others will be sacrificed at end stage disease using criteria for euthanasia. The latter cohorts will be followed temporally for behavioral analyses as well as survival.

Survival. Mice will be observed three times daily (morning, noon, and late afternoon) throughout the experiment. Mice will be euthanized when disease progression is sufficiently severe that they were unable to initiate movement and right themselves after gentle prodding for 30 seconds.

Body weights. Mice will be weighed twice a week at the same time each day. Weight loss is a sensitive measure of disease progression in transgenic G93A SOD1 mice and of toxicity in transgenic and wild type mice.

Motor/behavioral. Quantitative methods of testing motor function will be used including Rotarod and analysis of open field behavior. Decline of motor function is a sensitive measure of disease onset and progression. Behavioral testing for the transgenic G93A SOD1 mice will be performed during the light phase of the diurnal cycle since these mice are sufficiently active during that time. Measurements will be made for 30 minutes after 10 minutes of acclimation to the box (Opto-Varimex Unit, Columbus Instruments, Columbus, Ohio, USA). Counts of horizontal and vertical motion activity will be monitored and quantitative analysis of locomotor activity (resting and ambulatory times), will be assessed. The open field box will be cleaned before testing each mouse. Each 30 minutes of testing will be analyzed as three periods of 10 minute intervals to study the influence of novelty and measured behavior. Mice will be coded and investigators will be blinded to the genotype and analysis. Testing will start on week 4 and be performed every other week until the mice can no longer participate.

Neuropathology. Selected cohorts (n=10) of treated and untreated G93A SOD1 mice will be euthanized at 120 days for isolation and analysis of spinal cord tissue. For this purpose, mice will be deeply anesthetized and perfused transcardially with 4% buffered paraformaldehyde at the desired time point. These studies will be performed in a blinded manner, to avoid bias in interpretation of the results. Brains will be weighed, serially sectioned at 50 pm and stained for quantitative morphology (cresyl violet) to determine gross atrophy and identify ventral neuron loss and astrogliosis. Remaining tissue samples/sections will be stored for future use. Stereology will be used to quantify gross ventral horn atrophy, neuronal atrophy, and neuronal loss. Remaining tissue samples/sections will be stored for prospective mechanistic analyses as necessary.

Data sets will be generated and analyzed for each clinical and neuropathological measure. Effects on behavior and neuropathology will be compared in treatment and control groups. Dose-dependent effects will be assessed in each treatment group using multiple two sided ANOVA tests. Multiple comparisons in the same subject groups will be dealt with post hoc. Kaplan-Meier analysis will be used for survival and behavioral function.

Neuronal quantitation. Serial lumbar spinal cord tissue sections (n=20) from L3-L5 spinal cord segments will be used for gross spinal cord areas and neuronal analysis. Gross areas of the spinal cord sections will be quantified from each experimental cohort using NIH Image. From the same sections, the ventral horn will be delineated by a line from the central canal laterally and circumscribing the belly of gray matter. Absolute neuronal counts of Nissl-positive neurons will be performed in the ventral horns in the lumbar spinal cord. Only those neurons with nuclei will be counted. All counts will be performed with the experimenter (JM) blinded to treatment conditions. Counts will be performed using Image J (NIH) and manually verified and the data represent the average neuronal number from the sections used.

Example 5

Peripheral Administration of XPro1595 DN-TNF in a 3xTgAD Model of Alzheimer's Disease 3xTgAD mice are of a mixed 129/C57BL6 genetic background and will be generated. Animals will be housed in pathogen-free climate controlled facilities and allowed to have food and water ad libitum.

The mice will be injected with either 0.25 mg/kg (7.5x105 endotoxin units E.U./kg LPS (from *Escherichia coli* O111: B4; 3.0x106 E.U./mg, Sigma-Aldrich Corp., St. Louis, Mo.) or an equivalent volume of sterile saline (B. BraunMedical Inc., Bethlehem, Pa.). intraperitoneally (i.p.) twice weekly for 4 weeks. These two groups of mice will be further divided to receive peripheral administration of DN-TNF XPro1595 or formulation buffer. To evaluate the extent to which neutralization of solTNF in the periphery prevents the acceleration of AD-like pathology induced by chronic systemic inflammation in 3xTgAd mice, mice will be assessed for intraneuronal APP-derived 6E10 and C9-immunoreactive species.

Primary microglial cultures from 3xTgAD mice: Primary microglial cells will be isolated from postnatal day 1 (P1) 3xTgAD mouse pups and cultured as previously described (Saura et al., 2003). Quantification of activated microglia will be performed by counting the number of primary microglia that stained brightly positive for CD45 in 10 fields per well in 3 separate wells for each treatment condition. Total number of microglia will quantified by counting all cells stained positive for CD45 (strongly and weakly); these counts will be compared to the total number of nuclei counterstained with Hoechst 33258).

Fluorescence immunohistochemistry/immunocytochemistry: Immunohistochemistry will be performed on brain sections as previously described (McCoy et al., 2006). 10 μm cryosections will be incubated with mouse anti-human Aβ clone 6E10 (Chemicon Temecula, Calif., 1:3000). Immunoreactivity was visualized using an Alexa fluorconjugated secondary antibody, goat anti-mouse 488 (Molecular Probes/Invitrogen, Carlsbad, Calif., 1:1000). Sections will be counterstained with the nuclear dye Hoechst 33258 (bisbenzimide, 1:20,000). Immunocytochemistry will be performed as previously described (McCoy et al., 2006). Cells will be incubated with rabbit anti-NFκB p65 Rela (Santa Cruz Biotechnology, Santa Cruz, Calif., 1:200) or rat-anti-CD45 to visualize microglia (Serotec, 1:500) Immunoreactivity will be visualized using Alexa fluor-conjugated secondary antibodies (goat anti-rabbit 594 or goat anti-rat 594, 1:1000) followed by nuclear counterstain as above.

Brightfield immunohistochemistry/immunocytochemistry: Brain sections on slides will be stained using a previously published protocol (Frank et al., 2003). Epitope unmasking required for anti-Aβ (6E10), AB40- or 42-specific, and N-terminal APP staining consist of a brief incubation in 88% formic acid (Fisher Scientific, Fair Lawn, N.J.). 30 μm cryosections will be incubated with mouse anti-human Aβ clone 6E10 (1:1000), rabbit anti-human Aβ40 (Chemicon, 1:100), mouse anti-Aβ40 (Mab 13.1.1, 1:500, (Das et al., 2003; Kim et al., 2007), rabbit anti-human Aβ42 (Invitrogen, 1:100), mouse anti-Aβ42 (Mab 2.1.3, 1:500, (Das et al., 2003; Kim et al., 2007), rabbit anti-APP (C9, 1:500, (Kimberly et al., 2005), chicken anti-GFP (Chemicon, 1:500), rat anti-mouse CD68 (Serotec, 1:500), or rat antimouse CD45 (Serotec, 1:500), mouse anti-APP (22C11, 1:100, Chemicon). Sections will be then incubated with biotinylated secondary antibodies (horse anti-mouse, goat anti-rabbit, goat antichicken, or rabbit anti-goat, Vector Laboratories, Burlingame, Calif., 1:1000) followed by incubation with neutravidin-HRP (Pierce Biotechnology, Rockford, Ill.). Immunoreactivity will be visualized by reaction with diaminobenzidine (DAB) with nickel sulfate (to produce a purple-blue reaction product) or without ammonium nickel sulfate (to produce a brown reaction product).

Immunofluorescence confocal microscopy: 6-month old 3xTg-AD mice will be sacrificed by Euthasol overdose and cardiac perfusion with 0.01 M phosphate buffered saline (PBS). Brains will be rapidly removed, postfixed in 4% paraformaldehyde (pH-7.4) for 48 hr, and cut as 50 Pm thick coronal sections using a Vibratome. To examine intraneuronal Aβ, sections will be double-labeled with the monoclonal antibody 6E10 (Covance, Emeryville Calif.) and a polyclonal antibody directed against the C-terminus of amyloid precursor protein (APP) (Invitrogen). Primary antibodies will be applied overnight at 4° C. and following rinses will be detected with anti-mouse Alexa 555 (Invitrogen, 1:200, red) and anti-rabbit Alexa 488 (Invitrogen, 1:200, green). After rinsing, sections will be mounted on slides and coverslipped using Fluoromount-G (Southern Biotech). Specificity of all primary antibodies will be confirmed by Western blot and also by omission of primary antibody, which should demonstrate no staining. 6E10 recognizes amino acids 1-16 within the Aβ sequence and thus can also recognize full-length APP or the β-CTF of APP. Doublelabel confocal microscopy will therefore be utilize to identify interneuronal Aβ (red only) versus full-length APP or β-CTF immunoreactivity (overlap of red and green), or α-CTF (green only). Immunofluorescent sections will be visualized using a Bio-Rad 2100 confocal imaging system equipped with Argon, HeNe, and Red Diode lasers (Bio-Rad Laboratories, Hercules, Calif.). To avoid non-specific bleed-through, each laser line will be excited and detected independently using lambda-strobing mode. All images represent either single confocal Z-slices or Z-stacks. Kruskal-Wallis analysis will be performed to assess significance between experimental conditions.

Stereological analysis: Stereological analyses to estimate the number of amyloid-positive cells will be performed using the optical fractionator module of Stereoinvestigator software (MicroBrightField, Williston, Vt.). Contours will be traced around the hippocampus, cortex, and amygdala under the magnification of a 2× objective as delineated by the mouse brain atlas (Paxinos, 2001). Aβ positive (immunoreactive for 6E10) cells will be counted under a 60× oil immersion objective using random and systematic counting frames (size: 50 μm×50 μm) with an 18 um optical dissector, 2 μm upper and lower guard zones in a 430λ×280 μm grid.

Biochemical Analysis of Aβ40 and 42: Aβ from mouse brains will be extracted and measured as previously described (Levites et al, 2006). Briefly, each frozen hemi brain will be sequentially extracted in a two-step extraction involving, extraction in RIPA buffer followed by 70% formic acid. The following antibodies against Aβ will be used in sandwich capture ELISA for measuring Aβ levels as described before (Levites et al., 2006). For brain Aβ40, Ab9 (Aβ1-16) will be used for capture and Ab40.1-HRP for detection. For brain Aβ42, Ab42.2 was used for capture and Ab9-HRP for detection.

Immunoblot Analyses: Flash-frozen mouse hemispheres will be homogenized in ice-cold RIPA buffer with protease inhibitor cocktail (Roche, Indianapolis, Ind.). Protein samples will be diluted in 2× Laemmli sample buffer (62.5 mM Tris-HCl, pH 6.8, 20% glycerol, 2% SDS, 0.1% bromophenol blue, 5% 2-mercaptoethanol), boiled for 5 min, and run on a 4-20% Tris-Glycine gel(for PS1 and BACE1) or a 10-20% gel (APP and CTFs) for 90 min at 125V in 1× Tris-Glycine-SDS running buffer or 90 min at 130V in 1× Tricine-SDS running buffer. The gels will be transferred onto a 0.2 μm nitrocellulose membrane (Biorad) at 30V for 1 hr 30 min. The membranes will be blocked in 5% milk in TBST (1× TBS with 0.1% Tween-20) for 1 hour and incubated in primary antibodies (anti-APP C9, 1:500; anti-PS1, 1:2500; anti-BACE1, 1:1000; anti-alpha-tubulin, 1:5000) overnight at 4° C. The membranes will then be washed three times 10 min in TBST, incubated in secondary antibodies (goat-anti-mouse-HRP, 1:2500, or goat-anti-rabbit-HRP, 1:5000) for 1 hour at room temperature, then washed five times 10 min in TBST. The membrane will then be incubated for 1 min at room temperature in WestDura chemiluminescent substrate (Thermo Scientific, Rockford, Ill.) and imaged using the Chemilmager 5500 (Alpha Innotech, San Leandro, Calif.).

Example 6

Peripheral Administration of XPro1595 DN-TNF in a Rat Model of Neurotrauma

After blunt trauma to the skull or crush injury to the spine, these two groups of rats will be further divided to receive peripheral administration of DN-TNF XPro 1595 or formulation buffer to demonstrate control of neuroinflammation in the brain or improved recovery of the spine, respectively.

Example 7

Peripherally Administered XPro1595 Crosses the Blood Brain Barrier

Three groups of five mice each were treated as follows: 1) cuprizone-treated, XPro1595-treated, 2) naive, vehicle-treated, 3) naive, XPro1595-treated. Dosing protocol was 10 mg/kg twice a week subcutaneous for five weeks. Following administration of the treatments, brain and spinal cord were flushed out with PBS, blotted dry and frozen. The presence of XPro1595 in the brain was detected using an anti-human TNF-α antibody, which detects XPro1595 but does not cross react with endogenous mouse TNF-α.

As shown in FIG. 9, XPro1595 was detected in the brain and spinal cord of both naïve and cuprizone-treated mice, surprisingly demonstrating its ability to cross the blood-brain barrier in healthy animals having an intact blood brain barrier as well as in those animals where the blood brain barrier has been permeabilized by cuprizone intoxication.

All patents and patent publications referred to herein are hereby incorporated by reference. Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A method of treating a human patient with a neurological disorder of the central nervous system, comprising:

delivering a therapeutically effective amount of a PEGylated dominant negative TNF-α variant polypeptide to the patient by a peripheral route of administration, the PEGylated dominant negative TNF-α variant polypeptide being one that that crosses a blood brain barrier in the patient, whereby upon said peripheral administration the PEGylated dominant negative TNF-α variant polypeptide is delivered to the central nervous system of the patient;

wherein:

said PEGylated dominant negative TNF-α variant polypeptide comprises a variant sequence relative to wild-type TNF-α including the amino acid substitutions A145R/Y87H or A145R/I97T, said PEGylated dominant negative TNF-α variant polypeptide selectively binds one or two soluble TNF-α monomer units to form a TNF heterotrimer but does not inhibit signaling by transmembrane TNF-α, said PEGylated dominant negative TNF-α variant polypeptide does not comprise a fusion protein or antibody, and said PEGylated dominant negative TNF-α variant polypeptide is not immunosuppressive, whereby said patient is treated.

2. The method of claim 1, wherein said variant sequence further comprises the amino acid substitutions V1M/C69V/C101A/R31C.

3. The method of claim 1, wherein said PEGylated dominant negative TNF-α variant polypeptide comprises Xpro1595.

4. The method of claim 1, wherein said neurological disorder of the central nervous system is selected from the group consisting of multiple sclerosis, Parkinson's disease, Huntington's disease, amyotrophic lateral sclerosis (ALS), amyloidosis, stroke, depression and dementia.

5. The method of claim 4, wherein said amyloidosis is selected from the group consisting of Alzheimer's disease, frontotemporal dementia, and Lewy Body dementia.

6. A method of treating a human patient with a neurological disorder of the central nervous system, comprising:

delivering a therapeutically effective amount of a dominant negative TNF-α variant polypeptide to the brain of the human patient by peripherally administering the dominant negative TNF-α variant polypeptide, wherein said dominant negative TNF-α variant polypeptide comprises XPRO1595.

7. A method of treating a patient with neurological disorder comprising peripherally administering a therapeutically effective amount of a dominant negative TNF-α inhibitor, wherein the dominant negative TNF-α inhibitor comprises a variant sequence relative to wild-type TNF-α, the variant sequence comprising amino acid substitutions A145R/Y87H or A145R/I97T, whereby said patient is treated.

8. The method of claim 7, wherein the variant sequence further comprises amino acid substitutions V1M/C69V/C101A/R31C.

* * * * *

SEQUENCE LISTING

<160> NUMBER OF SEQ ID NOS: 9

<210> SEQ ID NO 1
<211> LENGTH: 495
<212> TYPE: DNA
<213> ORGANISM: Homo sapiens

<400> SEQUENCE: 1
atgcaccacc accaccacca cgtacgctcc tcctcccgca ctccgtccga caaaccggta 60
gctcacgtag tagctaaccc gcaggctgaa ggtcagctgc agtggctgaa ccgccgcgct 120
aacgctctgc tggctaacgg tgtagaactg cgcgacaacc agctggtagt accgtccgaa 180
ggtctgtacc tgatctactc ccaggtactg ttcaaaggtc agggttgtcc gtccactcac 240
gtactgctga ctcacactat ctcccgcatc gctgtatcct accagactaa agtaaacctg 300
ctgtccgcta tcaaatcccc gtgtcagcgc gaaactccgg aaggtgctga agctaaaccg 360
tggtacgaac cgatctacct gggtggtgta ttccagctgg aaaaaggtga ccgcctgtcc 420
gctgaaatca accgcccgga ctacctggac ttcgctgaat ccggtcaggt atacttcggt 480
atcatcgctc tgtga 495

<210> SEQ ID NO 2
<211> LENGTH: 164
<212> TYPE: PRT
<213> ORGANISM: Homo sapiens

<400> SEQUENCE: 2

Met His His His His His His Val Arg Ser Ser Ser Arg Thr Pro Ser
1 5 10 15

Asp Lys Pro Val Ala His Val Val Ala Asn Pro Gln Ala Glu Gly Gln
20 25 30

Leu Gln Trp Leu Asn Arg Arg Ala Asn Ala Leu Leu Ala Asn Gly Val
35 40 45

Glu Leu Arg Asp Asn Gln Leu Val Val Pro Ser Glu Gly Leu Tyr Leu
50 55 60

Ile Leu Ser Gln Val Leu Phe Lys Gly Gln Gly Cys Pro Ser Thr His
65 70 75 80

Val Leu Leu Thr His Thr Ile Ser Arg Ile Ala Val Ser Tyr Gln Thr
85 90 95

Lys Val Asn Leu Leu Ser Ala Ile Lys Ser Pro Cys Gln Arg Glu Thr
100 105 110

Pro Glu Gly Ala Glu Ala Lys Pro Trp Tyr Glu Pro Ile Tyr Leu Gly
115 120 125

Gly Val Phe Gln Leu Glu Lys Gly Asp Arg Leu Ser Ala Glu Ile Asn
130 135 140

Arg Pro Asp Tyr Leu Asp Phe Ala Glu Ser Gly Gln Val Tyr Phe Gly
145 150 155 160

Ile Ile Ala Leu

<210> SEQ ID NO 3
<211> LENGTH: 157
<212> TYPE: PRT
<213> ORGANISM: Homo sapiens

<400> SEQUENCE: 3

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Thr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 4
<211> LENGTH: 20
<212> TYPE: DNA
<213> ORGANISM: Mus musculis

<400> SEQUENCE: 4
gaagagtgtc ttgatgaaga 20

<210> SEQ ID NO 5
<211> LENGTH: 20
<212> TYPE: DNA
<213> ORGANISM: Mus musculus

<400> SEQUENCE: 5
gaaaagctgg atatgatagc 20

<210> SEQ ID NO 6
<211> LENGTH: 18
<212> TYPE: DNA
<213> ORGANISM: Mus musculus

<400> SEQUENCE: 6
gcgggctgcc tcgcagtc 18

<210> SEQ ID NO 7
<211> LENGTH: 20
<212> TYPE: DNA
<213> ORGANISM: Mus musculus

<400> SEQUENCE: 7
tcaccgcctt ggcttgtcac 20

-continued

```
<210> SEQ ID NO 8
<211> LENGTH: 20
<212> TYPE: DNA
<213> ORGANISM: Mus musculus

<400> SEQUENCE: 8

gacctgctcc acttctccag                                             20


<210> SEQ ID NO 9
<211> LENGTH: 21
<212> TYPE: DNA
<213> ORGANISM: Mus musculus

<400> SEQUENCE: 9

gggttcagac caagcgagaa g                                           21
```